(12) United States Patent
Hemmings et al.

(10) Patent No.: US 7,396,920 B2
(45) Date of Patent: Jul. 8, 2008

(54) TUMOUR SUPPRESSOR AND USES THEREOF

(75) Inventors: Brian A Hemmings, Bettingen (CH); Sauveur-Michel Maira, Habsheim (FR)

(73) Assignee: Novartis Forschungsstiftung Zweigniederlassung Friedrich Miescher Institute for Biomedical Research, Basel (CH)

( * ) Notice: Subject to any disclaimer, the term of this patent is extended or adjusted under 35 U.S.C. 154(b) by 652 days.

(21) Appl. No.: 10/297,641

(22) PCT Filed: Jun. 7, 2001

(86) PCT No.: PCT/EP01/06431

§ 371 (c)(1),
(2), (4) Date: Dec. 9, 2002

(87) PCT Pub. No.: WO01/94581

PCT Pub. Date: Dec. 13, 2001

(65) Prior Publication Data

US 2003/0124602 A1 Jul. 3, 2003

(30) Foreign Application Priority Data

Jun. 9, 2000 (GB) .................................. 0014185.3

(51) Int. Cl.
*C07H 21/04* (2006.01)
(52) U.S. Cl. ...................................... 536/23.1
(58) Field of Classification Search ........................ None
See application file for complete search history.

(56) References Cited

FOREIGN PATENT DOCUMENTS

| WO | WO 97 18303 | 5/1997 |
| WO | WO 99 58675 | 11/1999 |
| WO | WO 01/90304 | * 11/2001 |

OTHER PUBLICATIONS

Mol Cell Biol. Jan. 1999;19(1):777-87.*
Burgess et al., J of Cell Bio. 111:2129-2138, 1990.*
Lazar et al. Molecular and Cellular Biology 8:1247-1252, 1988.*
Bowie et al. Science, 247:1306-1310, 1990.*
Overbeek (1994, "Factors affecting transgenic animal production," Transgenic animal technology, pp. 96-98).*
(Wall, 1996 Theriogenology, vol. 45, pp. 57-68.*
Houdebine, 1994, J. Biotech. vol. 34, pp. 269-287.*
Kappell, 1992, Current Opinions in Biotechnology, vol. 3, pp. 548-553.*
Cameron, 1997, Molec. Biol. 7, pp. 253-265.*
Niemann, 1997, Transg. Res. 7, pp. 73-75.*
Mullins (1993, Hypertension, vol. 22, pp. 630-633).*
Mullins (1990, Nature, vol. 344, 541-544).*
Hammer (1990, Cell, vol. 63, 1099-1112).*
Mullins, 1989, EMBO J., vol. 8, pp. 4065-4072.*
Taurog, 1988, Jour. Immunol., vol. 141, pp. 4020-4023.*
Mullins (1996, J. Clin. Invest. vol. 98, pp. S37-S40.*
Filmus et al., "Development of Resistance Mechanisims to the Growth-Inhibitory Effects of Transforming Growth Factor-β During Tumor Progression", Current Opinion in Oncology, vol. 5, pp. 123-129, (1993).
Roberts et al., "Physiological Actions and Clinical Applications of Transforming Growth Factor-β (TGF-β)", Growth Factors, vol. 8, pp. 1-9, (1993).
Hanahan et al., "The Hallmarks of Cancer", Cell, vol. 100, pp. 57-70, (2000).
Vanhaeserbroech et al., "The PI3K-PDK1 connection: More than Just a Road to PKB", Biochem J. vol. 346, pp. 561-576, (2000).
Datta et al., "AKT Phosphorylation of Bad Couples Survival Signals to the Cell-Intrisic Death Machinery", Cell vol. 91, pp. 231-241, (1997).
Brunet et al., "Akt Promotes Cell Survival by Phosphorylating and Inhibiting a Forkhead Transcription Factor", Cell, vol. 96, pp. 857-868, (1999).
Kops et al., "Direct Control of the Forkhead Transcription Factor AFX by Protein kinase B", Nature, vol. 398, pp. 630-634, (1999).
Rena et al.. "Phosphorylation of the Transcription Factor Forkhead Family Member FKHR by Protein Kinase B", The Journal of Biological Chemistry, vol. 274, pp. 17179-17183, (1999).
Biggs, et al., "Protein Kinase B/Akt-Mediated Phosphorylation Promotes Nuclear Exclusion of the Winged Helix Transcription Factor FKHR1", Proc. Natl, Sci., USA, vol. 95, pp. 7421-7426, (1999).
Guo et al., "Phosphorylation of Serine 256 by Protein Kinase B Disrupts Transactivation by FKHR and Mediates Effects of Insulin on Insulin-Like Growth Factor-Binding Protein-1 Promoter Activity Through a Conserved Insulin Response Sequence", The Journal of Bio. Chem, vol. 274, No. 24 pp. 17184-17192, (1999).
Medema et al., "AFX Like Forkhead Transcription Factors Mediate Cell-Cycle Regulation by Ras and PKB Through P27$^{kip1}$", Nature, vol. 404, pp. 782-787, (2000).
Julian Downward, "Mechanisms and Consequences of Activation of Protein Kinase B/Akt", Current Opinion in Cell Biology, vol. 10, pp. 262-267, (1998).
Coffer et al., "Protein Kinase B(c-Akt): A Multifunctional Mediator of Phosphatidylinositol 3-Kinase Activation", Biochem J., vol. 335, pp. 1-13, (1998).
Kandel et al., "The Regulation and Activities of the Multifunctional Serine/Threonine Kinase Akt/PKB", Experimental Cell Research, vol. 253, pp. 210-229, (1999).
Frech et al., "High Affinity Binding of Inositol Phosphates and Phosphoinositides to the Pleckstrin Homology Domain of RAC/Protein Kinase B and Their Influence on Kinase Activity". The Journal of Biological Chem., vol. 272, No. 13, pp. 8474-8481, (1997).
Kavran et al., "Specificity and Promiscuity in Phosphoinositide Binding by Pleckstrin Homology Domains", The Journal of Biological Chemistry, vol. 273, No. 46, pp. 30497-30508, (1998).

(Continued)

*Primary Examiner*—Christopher Yaen
(74) *Attorney, Agent, or Firm*—Hoxie & Associates LLC; Thomas Hoxie; Brittany La

(57) ABSTRACT

A human protein (designated Carboxy-terminal Modulating protein, CTMP) is described and is identified as having tumour suppressor properties. CTMP has been shown to interact with protein kinase B and inhibit protein kinase B activity, establishing its importance in the protein kinase B signalling pathway.

5 Claims, 1 Drawing Sheet

OTHER PUBLICATIONS

Burgering et al., "Protein Kinase B (c-Akt) in Phosphatidylinositol-3-OH Kinase Signal Transduction", Nature, vol. 376, pp. 599-602, (1995).

Cross et al., "Inhibition of Glycogen Synthase Kinase-3 by Insulin Mediated by Protein Kinase B", Nature, vol. 378, pp. 785-789, (1995).

Franke et al., "The Protein Kinase Encoded by the Akt Proto-Oncogene is a Target of the PDGF-Activated Phosphatidylinositol 3-Kinase", Cell, vol. 81, pp. 727-736, (1995).

Kohn, et al, "Insulin Stimulates the Kinase Activity of RAC-PK, a Pleckstrin Homology Domain Containing Ser/Thr Kinase", The EMBO Journal, vol. 14, No. 7, pp. 4288-4295, (1995).

Alessi et al., "Mechanism of Activation of Protein Kinase B by Insulin and IGF-1", The EMBO Journal, vol. 15, pp. 6541-6551, (1996).

Kohn et al., "Akt, a Pleckstrin Homology Domain containing Kinase, Is Activated Primarily by Phosphorylation", The Journal of Biological Chemistry, vol. 271, pp. 21920-21926, (1996).

Andjelkovic et al., "Role of Translocation in the Activation and Function of Protein Kinase B", The Journal of Biological Chemistry, vol. 272, No. 50, pp. 31515-31524, (1997).

Bellacosa et al., "Structure, Expression and Chromosomal Mapping of c-akt: Relationship to v-akt and it's Implications", Oncogene, vol. 8, pp. 745-754, (1993).

Aoki et al., "The Akt Kinase; Molecular Determinates of Oncogenicity", Proc. Natl. Acad. Sci. USA, vol. 95, pp. 14950-14955, (1998).

Cantley et al., "New Insights into Tumor Suppression: PTEN Suppresses Tumor Formation by Restraining the Phosphoinositide 3-Kinase/AKT Pathway", Proc. Natl. Acad. Sci. USA, vol. 96, pp. 4240-4245, (1999).

Vazquez et al., the PTEN Tumor Suppressor Protein: An Antagonist of Phosphoinositide 3-Kinase Signaling, Biochimica et Biophysica Acta, vol. 1470, pp. M21-M35, (2000).

Alessi et al, "Characterization of a 3-Phosphoinositide-Dependent Protein Kinase Which Phosphorylates and Activates Protein Kianse Bα", Current Biology, vol. 7, pp. 261-269, (1997).

Stokoe et al., "Dual role of Phosphatidylinsoitol-3, 4, 5-Trisphosphate in the Activation of Protein Kinase B", Science, vol. 277, pp. 567-570, (1997).

Stephens et al., "Protein Kinase B Kinases That Mediate Phosphatidylinositol 3, 4, 5-Trisphosphate", vol. 279, pp. 710-714, (1998).

Balendran et al., "PDK1 Acquires PDK2 Activity in the Presence of a Synthetic Peptide Derived from the Carboxyl terminus of PRK2", Current Biology, vol. 9, pp. 393-404, (1999).

Biondi et al., "Identification of a Pocket in the PDK1 Kinase Domain that Interacts with PIF and the C-Terminal Residues of PKA", The EMBO Journal, vol. 19, pp. 979-988, (2000).

Toker et al., "Akt/Protein Kinase B is Regulated by Autophosphorylation at the Hypothetical PDK-2 Site", The Journal of Biological Chemistry, vol. 275, pp. 8271-8274, (2000).

W.K. Cavenee, "A Siren Song from Tumor Cells", J. Clin. Invest. vol. 91, pp. 3, (1993).

Brigid Hogan, "Enhancers, Chromosome Position Effects, and Transgenic Mice", Nature, vol. 306, pp. 313, (1983).

Coffer et al., "Molecular Cloning and Characterisation of a Novel Putative Protein-Serine Kinase Related to the cAMP-Dependent and Protein Kinase C Families", Eur. J. Biochem., vol. 201, pp. 475-481, (1991).

Chevray et al., "Protein Interaction Cloning in Yeast: Identification of Mammalian Proteins that React with the Leucine Zipper of Jun", Proc. Natl. Acad. Sci. USA, vol. 89, pp. 5789-5793, (1992).

Groves et al., "The Structure of the Protein Phosphatase 2A PR65/A Subunit Reveals the Conformation of it's 15 Tandemly Repeated Heat Motifs", Cell, vol. 96, pp. 99-110, (1999).

Hendrix et al., "Analysis of Subunit Isoforms in Protein Phosphatase 2A Holenzymes from Rabbit and *Xenopus*", The Journal of Biological Chemistry, vol. 268, No. 10, pp. 7330-7337, (1993).

Chen et al., "High Efficiency Transformation of Mammalian Cells by Plasmid DNA", Molecular and Cellular Biology, vol. 7, No. 8, pp. 2745-2752, (1987).

Fischer et al., "Rapid Actin-Based Plasticity in Dendritic Spines", Neuron, vol. 20, pp. 847-854, (1998).

Ponting et al., "PDZ Domains: Targeting Signalling Molecules to Sub-membranous Sites", BioEssays, vol. 19, No. 6, pp. 649-679, (1997).

Hartmut Oschkinat, "A New Type of PDZ Domain Recognition", Nature Structural Biology, vol. 6, No. 5, pp. 408-410, (1999).

Tochio et al., "Solution Structure of the Extended Neuronal Nitric Oxide Synthase PDZ Domain Complexed with an Associated Peptide", Nature Structural Biology, vol. 6 No. 5, pp. 417-421, (1999).

Hillier et al., "Unexpected Modes of PDZ Domain Scaffolding Revealed by Structure of nNOS-Syntrophin Complex", Science, vol. 284, pp. 812-815, (1999).

Yasukawa et al., "the JAK-Binding Protein JAB Inhibits Janus Tyrosine Kinase Activity Through Binding in the Activation Loop", The EMBO Journal, vol. 18, No. 5, pp. 1309-1320, (1999).

Chatton et al., "Eukaryotic GST Fusion Vector for the Study of Protein-Protein Associations In Vivo: Application to Interaction of ATFa with Jun and Fos", BioTechniques, vol. 18, No. 1, pp. 142-145, (1995).

Posner et al., "Preoxovanadium Compounds", The Journal of Biological Chemistry, vol. 269, No. 6, pp. 4596-4604, (1994).

Jones et al., "Molecular Cloning and Identification of a Serine/Threonine Protein Kinase of the Second-Messenger Subfamily", Proc. Natl. Acad. Sci. USA, vol. 88, pp. 4171-4175, (1991).

Staal et al., "Isolation of Transforming Murine Leukemia Viruses from Mice with a High Incidence of Spontaneous Lymphoma", Proc. Natl. Acad. Sci. USA, vol. 74, No. 7, pp. 3065-3067, (1977).

Stephen P. Staal, "Molecular Cloning of the AKT Oncogene and its Human Homologues AKT1 and AKT2: Amplification of AKT1 in a Primary Human Gastric Adenocarcinoma", Proc. Natl. Acad. Sci. USA, vol. 84, pp. 5034-5037, (1987).

Staal et al., "Thymic Lymphoma Induction by the AKT8 Murine Retrovirus", Journal of Experimental Medicine, vol. 167, pp. 1259-1264, (1988).

Brown et al., "Role for Phosphatidylinositol 3-Kinase in the Sorting and Transport of Newly Synthesized Lysosomal Enzymes in the Mammalian Cells", The Journal of Cell Biology, vol. 130, No. 4, (1995).

GeneExpress: *H sapiens* Partial cDNA Sequence : Clone 35A11; Version 1; ID HSB35A112 AC F00707, (1995).

"The FAPESP/LICR Human Cancer Genome Project: IL3-CT0219-280100-061-F06 CT0219 *Homo sapiens* cDNA, mRNA Sequence", ID AW604257 AC AW604257, (2000).

Neto et al., "QV4-LT0016-140200-105-F06 LT0016 *Homo sapiens* cDNA, mRNA Sequence", ID AW835661, AC AW835661, (2000).

Hillier et al., "ZD58C09.R1 Soares_Fetal_Heart_NbHH19W *Homo sapiens* cDNA Clone Image: 344848 5', mRNA Sequence", ID HS206363, AC W76206, (1996).

Rowen et al., "*Homo sapiens* Chromosome 15 Clone RP11-178D12 Map 15Q21.3, Complete Sequence", ID AC013355, AC AC013355, (1999).

Andjelkovic et al., "Activation and Phosphorylation of a Pleckstrin Homology Domain Containing Protein Kinase (RAC-PK/PKB) Promoted by Serum and Protein Phosphatase Inhibitors", Proc. Natl. Acad. Sci. USA, vol. 93, No. 12 pp. 5699-5704, (1996).

Galetic et al., "Mechanism of Protein Kinase B Activation by Insulin/Insulin-Like Growth Factor-1 Revealed by Specific Inhibitors of Phosophoinositide 3 Kinase-significance for Diabetes and Cancer", Pharmacol. & Ther. vol. 82, Nos. 2-3, pp. 409-425, (1999).

Maira et al., "CarboxylTerminal Modular Protein (CTMP), a Negative Regulator of PKB/Akt and v-Akt at the Plasma Membrane", Science, vol. 294, No. 5541, pp. 374-380, (2001).

Bleeker et al., U.S. Appl. No. 10/994,201, filed Nov. 22, 2004.

Bleeker et al., U.S. Appl. No. 11/273,436, filed Nov. 15, 2005.

* cited by examiner

A

```
GAATTCGGCACGAGCTAGAGCAAGCGCGGCCCCGCGGCCCGGAGCCATGCTGAGGAGCTGC
                                             M  L  R  S  C
GCCGCGCGCCTCCGCACGCTGGGGGCTCTGTGCCGGCCGCCAGTAGGCCGGCGCCTGCCGG
 A  A  R  L  R  T  L  G  A  L  C  R  P  P  V  G  R  R  L  P  G
GAAGCGAGCCGCGACCCGAGCTGAGGTCATTTTCTTCTGAGGAAGTCATTCTTAAGGACTG
   S  E  P  R  P  E  L  R  S  F  S  S  E  E  V  I  L  K  D  C
TTCTGTCCCCAACCCCAGCTGGAACAAGGACCTAAGACTGCTCTTTGACCAGTTTATGAAG
 S  V  P  N  P  S  W  N  K  D  L  R  L  L  F  D  Q  F  M  K
AAATGTGAAGATGGCTCCTGGAAACGTTTGCCTTCATATAAACGTACACCTACTGAATGGA
 K  C  E  D  G  S  W  K  R  L  P  S  Y  K  R  T  P  T  E  W  I
TTCAAGACTTCAAAACCCATTTTCTTGACCCAAAGCTTATGAAAGAAGAACAAATGTCACA
 Q  D  F  K  T  H  F  L  D  P  K  L  M  K  E  E  Q  M  S  Q
GGCCCAGCTCTTCACCAGAAGCTTTGATGATGGCCTGGGCTTTGAATACGTGATGTTCTAC
 A  Q  L  F  T  R  S  F  D  D  G  L  G  F  E  Y  V  M  F  Y
AATGACATTGAGAAAAGGATGGTTTGCTTATTTCAAGGAGGCCCTTACCTGGAAGGACCAC
 N  D  I  E  K  R  M  V  C  L  F  Q  G  G  P  Y  L  E  G  P  P
CTGGATTCATTCATGGAGGTGCCATTGCAACCATGATTGATGCTACTGTTGGTATGTGTGC
   G  F  I  H  G  G  A  I  A  T  M  I  D  A  T  V  G  M  C  A
AATGATGGCTGGGGAATCGTCATGACTGCCAATCTCAACATCAATTATAAAAGACCTATC
 M  M  A  G  G  I  V  M  T  A  N  L  N  I  N  Y  K  R  P  I
CCTCTTTGTTCTGTTGTTATGATAAATAGCCAACTTGATAAAGTTGAAGGAAGGAAATTTT
 P  L  C  S  V  V  M  I  N  S  Q  L  D  K  V  E  G  R  K  F  F
TTGTTTCCTGTAATGTTCAGAGTGTTGATGAGAAGACCCTATACTCAGAGGCGACAAGCTT
 V  S  C  N  V  Q  S  V  D  E  K  T  L  Y  S  E  A  T  S  L
ATTTATAAAGCTGAATCCTGCTAAAAGTCTGACATAAAGAGCTGCTGGTGAACTCCATCTC
 F  I  K  L  N  P  A  K  S  L  T  *
ATTCTCGCCCCTCCAGAAGAAGCAGTTGTCCCCCAAATACTCTGCTCCCTCACTGCTGAAT
CCCTGTAGGGAGAAGCCTGCCAACAGTGACCTTCCGAAACAGCCTTCTGAATACAAAGAGG
ATTCAGTTTCCATCTTCTCAACTTTTTAACACAGAAACACTTCCTGCGAGCATATCGACAA
CTCTCGGGCCAGGCGCTGTGGCTCACACCTGTAATCCCAGCACTTTAGGAGGCCGAGGCAG
GCGGATTGCCTGAGCTCAGGAGTTCAAGATCAGTCTGGGCAACACGATGAAACTCCGTCTC
TACTAAAATACAAAAAATTATCCAGGCATGGTGGCGTACGCCTGTAGTCCCAGCTACTCAG
GAGGCTGAGGCAGGAGAATTGCTTGAACCCAGGAGGAAGAGGTTGCAGTGAGCCAAGATCA
TGCCACATCACTCCAACCTGGGCAACAGAACAAGAACCCATCTCAAACAAAACAACAAACA
AAAAAAAAAAAAAAAACTCGAG
```

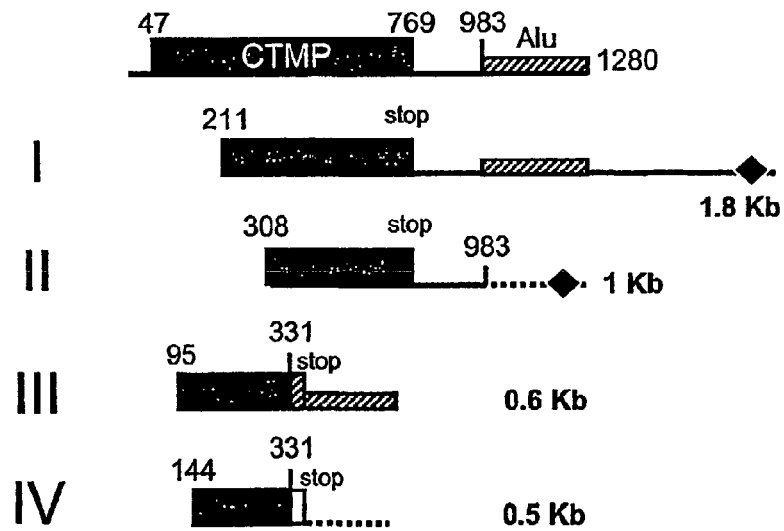

TUMOUR SUPPRESSOR AND USES THEREOF

The current invention relates to tumour suppressor genes and to the use of such genes and their protein products in identifying modulators thereof, and in cancer screening and therapy. More particularly, the present invention relates to the CTMP gene, the protein product of which interacts with protein kinase B (PKB), and to a method of identifying molecules involved in signal transduction.

BACKGROUND OF THE INVENTION

Reversible protein phosphorylation is a major mechanism for the coordinated control of many fundamental cellular functions in eukaryotic organisms, including metabolism, growth, and differentiation. The phosphorylation status, and consequently the activity, of specific target proteins is regulated by the opposing actions of protein kinases and protein phosphatases. Generally, these enzymes are specific either for serine/threonine or for tyrosine phosphoacceptors, although some dual specificity kinases and phosphatases have also been described. The importance of phosphorylation cascades is reflected by the finding that many kinases, phosphatases, and the signal transduction pathways in which they participate have been highly conserved during the course of evolution. In recent years, interest has focused on the role of protein phosphorylation in the control of the cell cycle; a number of cellular proto-oncogenes encode members of the serine/threonine kinase family and it has become increasingly clear that certain serine/threonine kinases function as key components of the cell cycle regulatory network. Therefore, the complete delineation of these pathways is an important aim for the understanding of oncogenesis and tumour progression.

Loss of sensitivity to negative growth regulators may be an important step in the development of malignant tumours. For example, transforming growth factor beta (TGFbeta), a potent natural antiproliferative agent, is believed to play an important role in suppressing tumorigenicity. Comparisons of human colon carcinoma and melanoma cell lines have demonstrated a progressive loss of responsiveness to the growth inhibitory effects of TGFbeta as tumour aggressiveness increases (Filmus et al., 1993, Curr. Opin. Oncol., 5, 123-129; Roberts et al., 1993, Growth Factors, 8, 1-9).

It has become increasingly clear over the last 10 years that the products of most of the genes involved in cellular transformation and cancer i.e. oncogenes and tumour suppressor genes are components of signal transduction pathways (Hanahan and Weinberg, 2000, Cell, 100, 57-70). As a result of extensive studies of the PI-3K/PKB signal transduction pathway, PKB was determined to play a major role in PI-3K induced signalling and involved in the regulation of various aspects of cellular processes (Galetic et al., 1999, Pharmacol. Ther., 82, 409-425; Vanhaesebroeck and Alessi, 2000, Biochem. J. 346 Pt 3, 561-576). For example, PKB regulates cell survival by phosphorylating and either activating the anti-apoptotic factor BAD (Datta et al., 1997, Cell, 91, 231-241), or inhibiting the pro-apoptotic and growth suppressor Forkhead transcription factors FKHR, FKHRL1 and AFX (Brunet et al., 1999, Cell, 96, 857-868; Kops et al., 1999, Nature, 398, 630-634; Rena et al., 1999, J. Biol. Chem., 274, 17179-17183; Biggs et al., 1999, Proc. Natl. Acad. Sci. USA, 96, 7421-7426; Guo et al., 1999, J. Biol. Chem., 274, 17184-17192; Medema et al., 2000, Nature, 404,782-787).

c-Akt/PKB is an ubiquitous Ser/Thr protein kinase which has a complex mechanism of regulation yet to be completely resolved (Downward et al., 1998, Curr. Opin. Cell Biol., 10, 262-267; Coffer et al., 1998, Biochem. J., 335, 1-13; Kandel and Hay, 1999, Exp. Cell Res., 253, 210-229; Vanhaesebroeck and Alessi, 2000). PKB is highly activated by the PI-3K-generated second messenger, phosphatidylinositol 3,4,5 phosphate (PI-3,4,5-P3), due to the presence at its N-terminus of a PH domain that has a high affinity for this lipid (Frech et al., 1997, J. Biol. Chem., 272, 8474-8481; Kavran et al., 1998, J. Biol. Chem., 273, 30497-30508). The use of the PI-3K specific inhibitors Wortmannin and LY294002 has clearly demonstrated that PKB, in-vivo, is a downstream target of PI-3K upon cell stimulation by a wide variety of stimuli such as PDGF, EGF, bFGF, serum, insulin and IGF-1 (Burgering and Coffer, 1995, Nature, 376, 599-602; Cross et al., 1995, Nature, 378, 785-789; Franke et al., 1995, Cell, 81, 727-736; Kohn et al., 1995, EMBO J., 14, 4288-4295; Alessi et al., 1996, EMBO J., 15, 6541-6551; Andjelkovic et al., 1996, Proc. Natl. Acad. Sci. USA, 93,5699-5704). These results suggested that PKB might be bound to the membrane for activation since PI-3,4,5-P3 is located in the plasma membrane. Indeed, after cell stimulation, PKB is effectively translocated from the cytoplasm to the membrane in a wortmannin-dependent manner (Kohn et al., 1996, J. Biol. Chem., 271, 21920-21926; Andjelkovic et al., 1997, J. Biol. Chem., 272, 31515-31524). The membrane localization of PKB for activation is further supported in that only a constitutively membrane-bound PKB, such as the retroviral oncogene v-Akt or a chimeric PKB with a myristoylation motif at its N-terminus are able to transform cells (Bellacosa et al., 1993, Oncogene, 8, 745-754; Aoki et al., 1998, Proc. Natl. Acad. Sci. USA, 95,14950-14955).

When bound to the plasma membrane, PKB is required to be phosphorylated on residues Thr308 (in the activation loop) and Ser473 (in the C-terminal regulatory domain) for full activation in a wortmannin-dependent manner (Alessi et al., 1996). In cells lacking the tumour suppressor PTEN (a lipid phosphatase), PKB is more active (Cantley and Neel, 1999, Proc. Natl. Acad. Sci. USA, 96, 4240-4245; Vazquez and Sellers, 2000, Biochim. Biophys. Acta, 1470, M21-M35), as a result of the increase in phosphorylation at these residues. The kinase PDK1, a kinase that contains a PH domain, has been shown to be able to phosphorylate PKB at Thr-308 in-vivo (Alessi et al., 1997, Curr. Biol., 7, 261-269; Stokoe et al., 1997, Science, 277, 567-570; Stephens et al., 1998, Science, 279, 710-714). Although PDK1 or even PKB itself can phosphorylate Ser473, the kinase responsible for Ser473 phosphorylation in vivo, often referred to as PDK2 or Ser473 kinase has not yet been identified (Balendran et al., 1999, Curr. Biol., 9, 393-404; Biondi et al., 2000, EMBO J., 19, 979-988; Toker and Newton, 2000, J. Biol. Chem., 275, 8271-8274).

The yeast two hybrid system (Fields and Song (1989) Nature 340, 245-246; Chien et al. (1991) Proc. Natl. Acad. Sci. USA 88, 9578-9582) has previously been used to determine if protein kinase B (PKB) could function by forming specific interactions with other proteins (PCT WO9718303). The existence of a PKB-interacting protein, Carboxy-Terminal Binding Protein (CTBP), was also described therein. For clarification, PKB was previously known as RAC-PK and AKT. Proteins and other factors that interact with PKB need to be identified to allow manipulation of PKB signalling pathways and their dependent cellular processes. The present invention relates to the identification of a novel PKB-interacting protein and its characterization as a tumour suppressor agent.

SUMMARY OF THE INVENTION

The present invention relates to a mammalian CTMP gene sequence and the characterisation of the CTMP protein encoded thereby. Thus, in one aspect of the invention, an isolated nucleic acid is provided comprising:

(i) a nucleotide sequence as shown in SEQ ID NO:1 encoding a carboxy-terminal modulating protein;

(ii) a nucleotide sequence encoding a carboxy-terminal modulating protein differing from SEQ ID NO:1 by codon usage;

(iii) a nucleotide sequence encoding a carboxy-terminal modulating protein homologue with at least 50% identity to SEQ ID No:2, said nucleotide sequence differing from SEQ ID NO:1 by having at least one inserted, deleted or altered codon;

(iv) a subsequence of any of the nucleotide sequences of (i), (ii) or (iii), with the proviso that said subsequence is not EST W76206, AA045430, F00707 or AA526313, or nucleotides −46-+65, preferably −45 to +73 of SEQ ID NO:1; or (v) a nucleotide sequence complementary to the nucleotide sequences of (i), (ii) or (iii), or complementary to the subsequence of (iv).

Also provided are recombinant vectors comprising the nucleic acids of the invention and host cells containing the nucleic acids or vectors of the invention.

In accordance with a further aspect of the invention, a substantially pure CTMP protein is provided comprising at least one functional domain of a CTMP protein or an antigenic determinant of a CTMP protein, as well as fusion proteins comprising CTMP protein sequences. The CTMP proteins of the invention typically have at least 50% identity, preferably at least 80% identity, more preferably at least 90% identity to the CTMP encoded by the nucleotide sequence of SEQ ID NO:1, or most preferably have the sequence of SEQ ID NO:2.

In accordance with a further aspect of the invention, a fragment of a CTMP protein is provided, which possesses an activity selected from the group consisting of protein kinase B binding activity, protein kinase B inhibiting activity and tumour suppressive activity.

In accordance with a further aspect of the invention, a method is provided for producing antibodies which selectively bind to a CTMP protein comprising the steps of:

(a) administering an immunogenically effective amount of a CTMP immunogen to an animal;

(b) allowing the animal to produce antibodies to the immunogen; and (c) obtaining the antibodies from the animal or from a cell culture derived therefrom.

In accordance with a further aspect of the invention, a substantially pure antibody is provided which binds selectively to an antigenic determinant of a CTMP protein.

With the identification of the gene sequence and the gene product, probes and antibodies raised to the gene product can be prepared and used in a variety of hybridization and immunological assays to screen for and detect the presence of either a normal or mutated gene or gene product. Thus, the present invention also provides screening assays using the probes and antibodies. In particular, the invention also relates to the identification of CTMP as a tumour suppressor. Thus, the invention allows screening for a predisposition to cancer or methods for the diagnosis/prognosis of cancer, as well as therapeutic methods for the treatment of cancer. The present invention also allows for the development of novel drugs to mimic the effect of the normal CTMP protein or for drugs used as modulators of the protein.

In accordance with a further aspect of the invention, a method is provided for suppressing the neoplastic phenotype of a cell comprising administering to the cell an agent selected from the group consisting of:

(a) a nucleotide sequence encoding a CTMP protein;

(b) CTMP protein, fragments, polypeptides and derivatives of polypeptides;

(c) a polynucleotide strand antisense to a mutant CTMP gene;

(e) an agent to stabilize CTMP protein; and (f) an agent to stimulate interaction of CTMP protein with PKB.

In accordance with a further aspect of the invention, a method is provided for identifying compounds modulating expression of a CTMP gene comprising:

(a) contacting a cell with a candidate compound wherein the cell includes a regulatory region of a CTMP gene operably joined to a coding region; and (b) detecting a change in expression of the coding region.

In accordance with a further aspect of the invention, a method is provided of screening for an agent useful in treating a disorder characterized by an abnormality in a PKB signalling pathway, wherein the pathway involves an interaction between a CTMP protein and a CTMP binding partner, such as PKB, comprising screening potential agents for ability to disrupt or promote the interaction as an indication of a useful agent. Agents determined to affect CTMP-PKB interactions are also encompassed by the invention.

In accordance with a further aspect of the invention, a method is provided of preventing or treating a disorder in a mammal characterized by an abnormality in a PKB signalling pathway, wherein the pathway involves an interaction between a CTMP protein and a CTMP binding partner, such as PKB, comprising the step of disrupting or promoting said interaction in vivo.

SUMMARY OF THE DRAWINGS

The invention, as exemplified by preferred embodiments, is described herein with reference to the accompanying drawings in which:

FIG. 1 depicts A Nucleotide and deduced amino acid sequence of the cDNA insert of pGADGH.CTMP. The 5' EcoRI cloning site and the 3' oligo-d(T)-XhoI primer are in bold text. The 3' ALU repeat sequence is in italics and underlined. The deduced amino acide sequence is shown in the one letter code. B The human ESTs homologous to CTMP cDNA. Homology searches in nucleotide databases with the CTMP cDNA detected 4 kinds of ESTs (I to IV). The stipled box represents an ALU repeat sequence. Black squares represent a poly-adenylation signal sequence. Dotted lines represent divergent sequences compared to the cloned CTMP cDNA.

The human CTMP cDNA is provided in SEQ ID NO:1 and deduced amino acid sequence is provided in SEQ ID NO:2.

DETAILED DESCRIPTION OF THE INVENTION

The present invention relates to Carboxy-Terminal Modulating Protein, CTMP, as well as homologues and derivatives thereof, and its characterization as a candidate tumour suppressor gene. CTMP protein is shown to inhibit phosphorylation of serine 473 of PKB, thereby inhibiting PKB's kinase activity. Furthermore, CTMP is demonstrated to have tumour suppressive function. Knowledge of the function of CTMP is useful in devising diagnostic and therapeutic strategies that are highly specific for neoplastic conditions.

Isolated Nucleic Acid

In accordance with a first aspect of the invention, an isolated nucleic acid is provided comprising a nucleotide sequence encoding CTMP protein, optionally comprising one or more introns. The polynucleotide may be in the form of DNA, genomic DNA, cDNA, mRNA or various fragments and portions of the gene sequence encoding CTMP. The CTMP encoding DNA is conserved in many species, including humans and rodents, for example mice.

A preferred DNA coding for the polypeptide of the invention is depicted in SEQ ID NO:1. The cDNA sequence of CTMP shown as SEQ. ID NO:1 contains the 5' and 3' untranslated regions (UTR) and encodes the entire open reading frame of CTMP. The coding region spans 720 nucleotides resulting in a predicted gene product of 240 amino acids (SEQ ID NO:2). The complete cDNA sequence allows one skilled in the art to develop useful related sequences, such as nucleotide sequences encoding carboxy-terminal modulating protein but differing from SEQ ID NO:1 by codon usage. It is known in the art that codon usage can affect expression levels depending on the host cell used.

In addition, a nucleotide sequence encoding a carboxy-terminal modulating protein homologue is provided, where the nucleotide sequence differs from SEQ ID NO:1 by having at least one inserted, deleted or altered codon but preferably not affecting CTMP's functional characteristics.

Probes and primers are also provided for the identification of homologous sequences, ie. sequences sharing sequence identity with SEQ ID NO:1, to screen for the transcription products of the protein of the invention in certain tissues or for the identification of mutations within the cDNA. Both 5' and 3' regions may also prove useful for providing binding sites for agents that may up- or down-regulate the gene, further delineating the function of CTMP, for example, in the PKB pathway. Fragments of the sequence (SEQ ID NO:1) encoding CTMP are encompassed by the invention with the proviso that the fragment is not EST W76206, M045430, F00707 or AA526313, or nucleotides −46 to +65, preferably −46 to +73 of SEQ ID NO:1. As is apparent to one of ordinary skill in the art, the first "A" of the "ATG" codon encoding the first amino acid of SEQ ID NO:2 is referred to as +1, other nucleotides are numbered consecutively from +1, with upstream sequences designated with a minus and downstream sequences designated with a plus. The fragments of the invention preferably encode fragments of CTMP, or functional domains, antigenic determinants or derivatives of CTMP.

Depending on the intended use, the invention provides portions of the disclosed nucleic acid sequences comprising about 10 consecutive nucleotides (e.g. for use as PCR primers) to nearly the complete disclosed nucleic acid sequence (SEQ ID NO:1). The invention provides isolated nucleic acid sequences comprising sequences corresponding to at least 10, preferably 15 and more preferably at least 20 or 50 consecutive nucleotides of the CTMP gene sequence or their complements. Nucleic acids may be produced synthetically using non-naturally occuring nucleotides, such as phosphothioates and the like, as is apparent to one of skill in the art.

Also provided are mutant sequences and portions of normal and mutant CTMP sequences. One of ordinary skill in the art is also now enabled to identify and isolate CTMP genes or cDNAs, which are allelic variants of the disclosed CTMP sequences, using standard hybridization screening or PCR techniques.

Thus, in accordance with one aspect of the invention, a method is provided for identifying allelic variants or heterospecific homologues of a CTMP gene comprising (a) choosing a nucleic acid probe or primer capable of hybridizing to a human CTMP gene sequence of the invention, preferably under stringent hybridization conditions;

(b) mixing said probe or primer with a sample of nucleic acids which may contain a nucleic acid corresponding to the variant or homologue; and (c) detecting hybridization of the probe or primer to the nucleic acid corresponding to the variant of homologue.

As is apparent to one of ordinary skill in the art, sequences complementary to all disclosed sequences are also provided.

In addition, the nucleic acids of the invention include any of the above described nucleotide sequences included in a vector. The DNA coding for the protein of the invention, as described above, may be comprised in a nucleic acid expression cassette comprising a promoter operably linked to a nucleic acid as defined above and optionally to transcription termination signals. Typical expression vectors contain promoters that direct the synthesis of large amounts of mRNA corresponding to the gene. They may also include sequences allowing for their autonomous replication within the host organism, sequences that encode genetic traits that allow cells containing the vectors to be selected, and sequences that increase the efficiency with which the mRNA is translated. Stable long-term vectors may be maintained as freely replicating entities by using regulatory elements of viruses. Cell lines may also be produced which have integrated the vector into the genomic DNA and in this manner the gene product is produced on a continuous basis. A relatively simple *E. coli* expression system utilizes the lac promoter and a neighbouring lacZ gene which is cut out of the expression vector with restriction enzymes and replaced by the CTMP gene sequence.

The promoter can be of almost any origin. It is for example possible to use a tightly regulated promoter or the promoter that is naturally adjacent to the CTMP gene. Preferred are promoters that are active in the chosen host cells like the SV40, tac, beta-actin, metallothionein, T7, polyhedrin and cytomegalovirus promoters.

A DNA sequence containing the transcription termination signals is preferably the 3' flanking sequence of a gene that contains proper signals for transcription termination and polyadenylation for the desired host. Suitable signals are, for example, the polyadenylation signal of the human growth hormone, of the DHFR gene and of the rabbit beta-globin gene.

It is also possible to use a polypeptide expression cassette additionally containing a signal sequence that causes the protein to be secreted into the medium, for example, for purification. Suitable signal sequences are known in the art. Accordingly, in these kinds of expression cassettes a promoter is operably linked to a first DNA sequence encoding a signal peptide linked in the proper reading frame to a second DNA sequence coding for the polypeptide of the invention, and a DNA sequence containing transcription termination signals.

The promoter, the DNA sequence coding for the protein of the invention and the DNA sequence containing transcription termination signals are operably linked to each other, i.e., they are juxtaposed in such a manner that their normal functions are maintained. The array is such that the promoter effects proper expression of the structural gene and the transcription termination signals effect proper termination of transcription and polyadenylation. The junction of these sequences may, for example, be effected by means of synthetic oligodeoxynucleotide linkers carrying the recognition sequence of an endonuclease.

It is likewise possible that the expression plasmids according to the invention include one or more, especially one or two, selective genetic markers for the host used for the construction, amplification and test of the plasmid, such a marker and an origin of replication for a bacterial host, especially *Escherichia coli*. As to the selective gene markers, any marker gene can be used which facilitates the selection for transformants due to the phenotypic expression of the marker gene. Suitable markers are, for example, those expressing antibiotic resistance or, in the case of auxotrophic host mutants, genes which complement host lesions. Corresponding genes confer, for example, resistance to the antibiotics tetracycline, ampicillin, G418, hygromycin or bleomycin or provide for prototrophy in an auxotrophic mutant, for example the URA3, LEU2, LYS2, HIS3 or TRP1 gene.

As the amplification of the expression plasmids is usually done in a prokaryote, such as *E. coli*, a replication origin is included advantageously. This can be obtained from corresponding prokaryotic plasmids, for example *E. coli* plasmids, such as pBluescript® pBR322, pTZ18R, or a pUC plasmid, for example pUC18 or pUC19, which contain both prokaryotic, e.g. *E. coli*, replication origin and genetic marker conferring resistance to antibiotics, such as ampicillin and tetracycline.

Apart from the polypeptide expression cassette, replication origin(s) and genetic marker(s) the expression plasmids according to the invention can contain optionally additional expression cassettes, such as 1 to 3 additional polypeptide expression cassettes, which may be the same or different.

The expression plasmids according to the invention are prepared by methods known in the art, for example by linking the polypeptide expression cassette, the DNA fragments containing selective genetic markers for the host used in the test and optionally for a bacterial host, the origin(s) of replication, and the optionally additional polypeptide expression cassettes in the predetermined order using conventional chemical or biological in vitro synthesis procedures. Preferably, the plasmids are constructed and prepared using recombinant DNA techniques. For the preparation by recombinant DNA techniques suitable DNA fragments are ligated in vitro in conventional manner. The ligation mixture is then transformed into a suitable prokaryotic or eukaryotic host depending on the nature of the regulatory elements used, and a transformant containing the desired vector is selected according to conventional procedures. The plasmids can be multiplicated by means of the transformed hosts and can be isolated in conventional manner. The choice of the host depends on the regulatory sequences located on the vector. For the construction and multiplication of the vector a prokaryotic host, e.g. *E. coli*, is preferred. The expression cassettes according to the invention may be inserted into the desired host in form of a stable plasmid or directly into the chromosome.

Hosts, Transfection and Culturing

Thus, the nucleic acid sequences are also useful for protein expression in appropriate vectors and hosts to produce CTMP protein. A suitable host for the production of the polypeptide of the invention is a eukaryotic or prokaryotic cell, for example a plant, mammalian, nematode, insect, yeast or bacterial cell. In particular, the host cell may be selected from the group consisting of *E. coli*, Pseudomonas, *Bacillus Subtilis*, or other bacilli, other bacteria, yeast, fungi, insect (using baculoviral vectors for expression), mouse or other animal or human tissue cells. Mammalian cells can also be used to express the CTMP protein using a vaccinia virus expression system, for example.

The suitable host, as defined above, can be transfected by the standard methods in genetic engineering, including, for example, calcium phosphate transfection, DEAE-dextran transfection, electroporation, microinjection, protoplast fusion, liposome-mediated transfection, viral infection. To increase the amount of protein produced, it is advantageous to use a high copy plasmid or the plasmid DNA is integrated into the genome in several copies. The latter can be achieved, for example, through applying a selective stress, e.g., using methotrexate. The transfected host cells can be cultured by standard methods in cell culture.

Eukaryotic expression systems permit appropriate post-translational modifications of expressed proteins. This allows for studies of the CTMP gene and gene product including determination of proper expression and post-translational modifications for biological activity, identifying regulatory elements in the 5' region of the gene and their role in tissue regulation of protein expression. It also permits the production of large amounts of normal and mutant proteins for isolation and purification, the use of cells expressing CTMP as a functional assay system for antibodies generated against the protein, the testing of the effectiveness of pharmacological agents or to increase or decrease the activity of CTMP, and the study of the function of the normal complete protein, specific portions of the protein, or of naturally occurring polymorphisms and artificially produced mutated proteins.

In order to produce mutated or polymorphic proteins, the CTMP DNA sequence can be altered using procedures such as restriction enzyme digestion, DNA polymerase fill-in, exonuclease deletion, terminal deoxynucleotide transferase extension, ligation of synthetic or cloned DNA sequences and site-directed sequence alteration using specific oligonucleotides together with PCR. Alteration of the cDNA will allow for the production of specific mutations within cDNA sequence in order to express the created mutated proteins and study their biological effects.

Accordingly, a further embodiment of the current invention concerns a process for the production of the polypeptide of the invention comprising culturing a transfected host as defined above and isolating the polypeptide produced thereby.

The DNA coding for the polypeptide of the invention may be used also for the design of antisense RNA or DNA to inhibit the translation of CTMP in the organism, e.g., in order to influence effects that may be caused by an overexpression or deregulation of the natural CTMP, as well as to target factors which themselves influence CTMP.

The characteristics and function of the cloned CTMP cDNA sequence may be analyzed by introducing the sequence into various cell types. The function of the CTMP may then be examined under different physiological conditions. The CTMP sequence may be manipulated to understand the expression of the gene and gene product. Alternatively, cell lines may be produced which overexpress the gene product allowing purification of CTMP for biochemical characterization, large-scale production, antibody production and therapy.

CTMP Polypeptides and Peptides

CTMP and its homologues are polypeptides that share sufficient similarities for the skilled person to determine that they share homology of origin or function with CTMP as represented by human CTMP (SEQ ID NO:2). Species homologues from other organisms may be isolated according to the methods set out herein, which are conventional. Moreover, suitable alternative methods are known to those of skill in the art and may be found in the literature. Species homologues of CTMP may be considered derivatives of the polypeptide sequences set out herein.

In a preferred case, homology is used herein to refer to sequence identity. Thus, homologues are also polypeptides that share a certain amount of sequence identity with CTMP as herein described. Preferably, the sequence identity is at least 50%, more preferably at least 80%, yet more preferably at least 90% and most preferably at least 95% or more. Where amino acid residues in members of the CTMP are not identical, they may be similar, wherein the substitutions present are preferably conservative substitutions or alterations that do not alter the structure/function relationship of the domains of the protein.

Derivatives of said polypeptides, which form part of the present invention, also comprise mutants and fragments of CTMP. A mutant is a polypeptide that has, for example, one or more amino acid deletions, additions and/or substitutions, that is devoid of a certain domain or that is connected to another polypeptide, e.g., in form of a fusion protein, with the proviso that said fusion protein is not CTBP (WO97/18303). A mutant according to the invention still reacts comparably to the natural CTMP, e.g., in respect to the PKB binding specificity; thus, although its overall activity may be modulated or altered in minor ways, CTMP and mutants thereof are essentially functionally equivalent.

Fragments of CTMP comprise the CTMP polypeptide, or a mutant thereof, in which a substantial part of the polypeptide has been removed. Fragments of CTMP may have a substantially different activity to natural CTMP. Useful CTMP fragments may vary from about 4 to 5 amino acids (e.g. for use as immunogens) to the complete amino acid sequence of the CTMP proteins. The invention provides substantially pure polypeptides or peptides comprising sequences corresponding to preferably at least 5, more preferably at least 10 and most preferably at least 50 or 100 consecutive amino acids of the CTMP proteins. A fragment of a CTMP preferably possesses an activity selected from the group consisting of CTMP-specific antibody binding activity, protein kinase B binding activity, protein kinase B inhibiting activity and/or tumour suppressive activity.

Also encompassed by the invention are modififed CTMP, preferably phosphorylated CTMP or phosphorylated fragments thereof. Tryptic phosphopeptide mapping and/or mass spectrohpotometry can be carried out to determine whether CTMP is phosphorylated in vivo or in vitro. Phosphoamino acid analysis of in vitro or in vivo labelled protein reveals which residues are phosphorylated, such as phosphoserine and phosphothreonine residues. The present inventors have demonstrated that phosphorylation of one or more serine residues in SFSSEEVILK, in particular Ser-35 and to a lesser extent Ser-37 (the first and second serine residues in this sequence) potentially influences CTMP activity in vivo (see Example 8). In addition, the present inventors have demonstrated that a peptide comprising the last three amino acids of SEQ ID NO:2 is phosphorylated, and further identified the phosphorylation site as Ser-238. Thus, a mutation at one or more of these sites in CTMP or a fragment of CTMP including these sites, in particular to replace the serine with a negatively charged residue, can be particularly useful.

If the polypeptide of the invention is expressed in the form of a fusion protein, the fused polypeptides may be connected directly or by a spacer. It is for example possible to insert, if not already naturally present, a region that can be specifically recognised and cleaved chemically or enzymatically. Examples for selective cleaving reagents or enzymes are CNBr, V8 protease, trypsin, thrombin, factor X. Methods for the construction of fusion proteins, mutations or fragments by recombinant or chemical techniques are known in the art.

Isolation

Isolated proteins, or fragments thereof can be used for the generation of antibodies, in the identification of proteins that may bind to CTMP or for diagnostic or therapeutic methods and assays. Full length proteins and fragments of at least 4 amino acids may be isolated and purified for various applications. Phospho-specific antibodies can also be prepared by routine methods known in the art.

CTMP proteins, fragments of the proteins and fusion proteins can be isolated from natural sources by conventional means, from tissues or from cultured cells. The CTMP protein may be purified from tissues in which there is a high level of expression of the protein or it may be made by recombinant techniques as described above. During the isolation conventional additives like protein stabilisers, inhibitors of proteinases and the like may be added. For example, when the polypeptide is isolated from tissue culture, the first step consists usually in lysing the cells or, in the case where the polypeptide is secreted into the medium, in separating the cells from the culture fluid by means of centrifugation. In the presence of additional proteins and impurities, the resulting supernatant can be enriched for the polypeptide of the invention, e.g., by treatment with polyethyleneimine so as to remove most of the non-proteinaceous material, and precipitation of proteins by saturating the solution with ammonium sulphate or the like. Host proteins, if present, can also be precipitated by means of acidification with acetic acid and other conventional means.

Other purification steps may include, for example, removing the lectins, desalination, chromatographic processes, such as ion exchange chromatography, gel filtration chromatography, partition chromatography, immunoaffinity chromatography, high-performance liquid chromatography (HPLC), reversed phase HPLC (RP-HPLC), ion-exchange HPLC, size-exclusion HPLC, high-performance chromatofocusing and hydrophobic interaction chromatography or by precipitation (immunoprecipitation or immunoaffinity SDS-PAGE and PAGE). Polyacrylamide gel electrophoresis can also be used to isolate the CTMP protein based on its molecular weight, charge properties and hydrophobicity. The separation of the constituents of the mixture is also effected by dialysis, according to charge by means of gel electrophoresis or carrier-free electrophoresis, according to molecular size by means of a suitable Sephadex column, gel-permeation or ultrafiltration, by affinity chromatography, or by other processes, especially those known from the literature.

Similar procedures to those described above may be used to purify the protein from recombinant expression systems. For protein expression, eukaryotic or prokaryotic expression systems may be generated in which the CTMP gene sequence, cDNA or genomic, is introduced into a plasmid or other expression vector which is then introduced into living cells. Constructs in which the CTMP cDNA sequence containing the entire open reading frame inserted in the correct orientation into an expression plasmid may be used for protein expression. Alternatively, portions of the normal or mutant CTMP sequences may be inserted, optionally operably linked to other protein coding sequences to produce fusion proteins, such as CTMP-glutathione-S-transferase (GST) fusion proteins. The fusion protein can also be purified by affinity chromatography based upon the non-CTMP sequence and, optionally, the CTMP protein separated from the non-CTMP sequence by enzymatic cleavage of the fusion protein.

The polypeptide, and especially its derivatives, may be obtained by synthetic means rather than derived from natural or recombinant sources. Thus, using the information contained herein, CTMP polypeptide may be synthesised using commercially available protein synthesisers or even ordered from a commercial peptide synthesis service. Synthesised derivatives of CTMP may comprise any desired sequence modifications, including the use of altered amino acid residues or the addition of heterologous groups or side-chains to the polypeptide.

Antibodies

The proteins, fragments and fusion proteins also have utility, as described herein, for the preparation of polyclonal and monoclonal antibodies to normal and mutant CTMP proteins, for the identification of binding partners of the CTMP proteins and for diagnostic and therapeutic methods, as described herein. Thus, a further embodiment of the invention concerns antibodies that are specific for CTMP, especially human CTMP. Such antibodies may be useful for identifying or isolating CTMP, for example by immunostaining or immunoseparation, or for disrupting CTMP activity in vivo or in vitro.

CTMP-specific antibodies may be prepared according to techniques known in the art, as well as phospho-specific antibodies specifically recognizing phosphorylated CTMP or a phosphorylated fragment thereof. In order to prepare a polyclonal serum, for example, an antigenic portion of CTMP, consisting of a peptide derived therefrom, such as a C-terminal peptide, or a phosphopeptide comprising one or more of Ser35, Ser 37 and Ser238, or even the whole protein, optionally in the presence of an adjuvant or conjugated to an immunostimulatory agent such as keyhole limpet haemocyanin, is injected into a mammal such as a mouse or a rabbit. Typically, following booster injections at weekly intervals, the animals are then bled and the sera isolated. The sera can be used directly or purified prior to use by various methods including affinity chromatography employing Protein A-Sepharose, Antigen Sepharose or Anti-mouse-Ig-Sepharose, to give polyclonal antibodies.

When synthetic peptides are used to prepare antibodies, the most common practice is to choose a 10 to 15 amino acid residue peptide corresponding to the carboxyl or amino terminal sequence of a protein antigen, and to chemically cross-link it to a carrier molecule such as keyhole limpet hemocyanin or BSA. However, if an internal sequence peptide is desired, selection of the peptide is based on the use of algorithms that predict potential antigenic sites or other desired characteristics, such as peptides comprising one or more of Ser-35, Ser-37 and Ser-238. The algprothms are typically based on predictions of hydrophilicity (Kyte and Doolittle, 1982, J. Mol. Biol., 157, 105-132; Hopp and Woods, 1983, Mol. Immunol., 20, 483-489) or secondary structure (Chou and Fasman, 1978a, Annu. Rev. Biochem., 47, 251-276; Chou and Fasman, 1978b, Adv. Enzymol. Relat. Areas Mol. Biol., 47, 45-148). The objective is to choose a region of the protein that is either surface exposed, such as a hydrophilic region, or is conformationally flexible relative to the rest of the structure, such as a loop region or a region predicted to form a beta-turn. The selection process may also be limited by constraints imposed by the chemistry of the coupling procedures used to attach peptide to carrier protein.

Carboxyl-terminal peptides are frequently chosen because these are often more mobile than the rest of the molecule and the peptide can be coupled to a carrier in a straightforward manner using glutaraldehyde. The amino-terminal peptide has the disadvantage that it may be modified post-translationally by acetylation or by the removal of a leader sequence. Thus, the use of the amino-terminal sequences of CTMP is not preferred for the preparation of antibodies according to the invention, unless the peptide is produced by chemical synthesis. It should be noted that a comparison of the protein amino acid sequence between species can yield important information. Those regions with sequence differences between species are more likely to be immunogenic.

Monoclonal antibodies may be prepared according to similar established procedures. Truncated versions of monoclonal antibodies may also be produced by recombinant techniques in which plasmids are generated which express the desired monoclonal antibody fragment(s) in a suitable host.

Antibodies specific for mutagenised epitopes can also be generated. These antibodies are especially useful in cell culture assays to screen for malignant cells, expressing mutant CTMP, at different stages of malignant development. Such antibodies are also useful for screening malignant cells that have been treated with pharmaceutical agents in order to evaluate the therapeutic potential of the pharmaceutical agent. CTMP antibodies are also useful for detecting both normal and mutant proteins in cell culture, and transfected cell cultures expressing normal or mutant CTMP protein as well as for Western blot analysis on protein extracts of such cells.

Antibodies are also useful in various immunoassays for detecting and quantitating relative amounts of wild type or mutant protein. Enzyme-linked immunosorbant assays (ELISA) may be used to detect both wild type and mutant CTMP as well as antibodies generated against these proteins. Commonly used ELISA systems are indirect ELISA to detect specific antibodies, direct competitive ELISA to detect soluble antigens, antibody-sandwich ELISA to detect soluble antigens and double antibody-sandwich ELISA to detect specific antibodies.

Antibodies to CTMP may also be used for coupling to compounds such as radionuclides or fluorescent compounds, or to liposomes for diagnostic imaging and therapy, in order to target compounds to a specific tissue location. This is especially valuable for the specific targeting of malignant tissues with anti-cancer drugs, which would be detrimental to normal cells and tissues.

For a review of methods for preparation of antibodies, see Antibody Engineering: A Practical Guide, Barreback, ed., W. H. Freeman & Company, N.Y. (1992) or Antibody Engineering, 2nd Ed., Barreback, ed., Oxford University Press, Oxford (1995).

Cellular Distribution of CTMP in Malignant and Normal Tissues

The cellular distribution of CTMP in malignant and normal tissues may be analyzed by reverse transcriptase PCR analysis (see Example 2). In order to define the cellular distribution of CTMP, antibodies can be raised against both normal and mutant CTMP proteins. Such antibodies can then be used in both immunocytochemistry and immunofluorescence techniques to visualize the protein directly in cells and tissues in order to establish the subcellular localization of normal and mutant proteins.

In situ hybridization is another method that may be used to detect the expression of normal and mutant CTMP. In situ hybridization relies upon the hybridization of a specifically labelled nucleic acid probe to the cellular RNA in individual cells or tissues. Therefore, it allows the identification of mRNA within intact tissues. In this method, oligonucleotides corresponding to unique portions of the CTMP gene, normal or mutant, are used to detect specific mRNA species in the tissue of interest.

Diagnostics

The present inventors have determined that CTMP has an inhibitory effect on PKB kinase actvity (Example 9), that CTMP expression reverts PKB-transformed cells into a non-transformed phenotype (Example 11) and that CTMP expression inhibits tumorigenic properties of PKB-transformed cells in nude mice (Example 12). These findings indicate that CTMP is a tumour suppressor gene. Mutations might be acquired in cancerous cells in this gene function to disrupt PKB signalling. Tumour suppressor genes are often inactivated when one allele acquires a somatic mutation and the second allele is lost, typically through deletion (Cavenee et al., 1993, J. Clin. Invest., 91, 3). It is anticipated that missense mutations will be found in CTMP sequences from malignant tissues. Each of the mutations identified or a combination of mutations may be responsible for the development of cancer. It is also possible that other types of mutations may also be found such as any form of nucleotide sequence substitution, insertion or deletion that leads to changes in the predicted amino acid sequence or that leads to aberrant transcript processing, level or stability. Thus, CTMP gene mutations, deletions or amplifications may be implicated in the progression of numerous human tumours and provide methods for early diagnosis and/or prognosis of cancer.

The CTMP gene and gene product, as well as the CTMP-derived probes, primers and antibodies are useful in the screening for a predisposition to cancer, for the diagnosis and/or prognosis of cancer, and for the treatment of individuals with cancer. Individuals at risk of developing cancer, such as those individuals with a history of cancer in their families, or individuals not previously known to be at risk, may be routinely screened using probes to detect the presence of a mutant CTMP gene or protein (or other anomaly) by a variety of techniques. Diagnosis of inherited cases of these diseases can be accomplished by methods based upon the nucleic acid (including mRNA/cDNA and, preferably, genomic sequences), proteins, and/or antibodies specific for CTMP, including functional assays designed to detect failure or augmentation of the normal CTMP activity (such as PKB binding) and/or the presence of specific new activities conferred by mutant CTMP.

Preferably, the methods and products are based upon the human CTMP nucleic acids, protein or antibodies. The diagnostic and prognostic methods of the invention, therefore comprise detecting a mutation, deletion or amplification in a CTMP gene or gene product, where the deletion, mutation or amplification does not typically occur in normal cells. It is apparent to one of ordinary skill in the art that the methods are most useful for identifying individuals at risk of developing cancer and other methods can be used to confirm the diagnosis. Typically, data will be compared to standard observations, such as CTMP nucleic acids or gene products from normal cells or cells known to be cancerous.

Thus, in accordance with one aspect of the invention, a diagnostic method is provided for determining if a subject carries a mutant CTMP gene comprising the steps of
a) providing a biological sample from the subject; and
b) detecting in the sample a mutation on the CTMP nucleic acid, a mutant CTMP protein, or a mutant CTMP activity.

Any biological or clinical sample can be used for the diagnostic methods of the invention where CTMP expression is expected, including body fluids, tissue biopsies, surgical specimens, or autopsy material.

When a diagnostic assay is to be based upon the CTMP protein, a variety of approaches is possible. For example, diagnosis can be achieved by monitoring differences in the electrophoretic mobility of normal and mutant proteins. Alternatively, diagnosis may be based upon differences in the proteolytic cleavage patterns of normal and mutant proteins, differences in molar ratios of the various amino acid residues, or by functional assays demonstrating altered function of the gene products. In preferred embodiments, protein-based diagnostics will employ differences in the ability of antibodies to bind to normal and mutant CTMP proteins. Such diagnostic tests may employ antibodies which bind to the normal proteins but not to mutant proteins, or vice versa.

When the diagnostic assay is to be based upon nucleic acids from a sample, the assay may be based upon mRNA, cDNA or genomic DNA. Whether mRNA, cDNA or genomic DNA is assayed, standard methods well known in the art may be used to detect the presence of a particular sequence either in situ or in vitro (see, e.g., Sambrook et al., 1989, Molecular Cloning: A Laboratory Manual, 2nd Ed., Cold Spring Harbor Press, Cold Spring Harbor, N.Y.). As a general matter, however, any tissue with nucleated cells may be examined. DNA may be isolated and used directly for detection of a specific sequence or may be amplified by the polymerase chain reaction (PCR) prior to analysis. To detect a specific nucleic acid sequence, direct nucleotide sequencing, hybridization using specific oligonucleotides, restriction enzyme digest and mapping, PCR mapping, RNase protection, chemical mismatch cleavage, ligase-mediated detection, and various other methods may be employed. Oligonucleotides specific to particular sequences can be chemically synthesized and labeled radioactively or nonradioactively (e.g., biotin tags, ethidium bromide), and hybridized to individual samples immobilized on membranes or other solid-supports (e.g., by dot-blot or transfer from gels after electrophoresis), or in solution. The presence or absence of the target sequences may then be visualized using methods such as autoradiography, fluorometry, or colorimetry. These procedures can be automated using redundant, short oligonucleotides of known sequence fixed in high density to silicon chips.

Particularly contemplated as useful primers and probes will be sequences including nucleotide positions from the CTMP genes in which disease-causing mutations are known to be present, including introns and 5' and 3' UTRs, which may be shown to be associated with the development of malignancy, or sequences which flank these positions. Primers may be chosen for specific CTMP mutations or for the mutational "hot spots" in general. It should also be noted that the probes and primers may include specific mutated nucleotides.

Use of CTMP and Therapy

Kinases such as PKB are known to be involved in signal transduction within cells. This involvement makes kinases targets for agents that seek to obtain a biological effect by modulating a signalling pathway. Typically, modulation of a signalling pathway will alter the response of a cell to a particular stimulus. For example, the effect of hormones may be modulated by targeting the kinases involved in signal transduction from the hormone receptor to the biological effectors, which are typically regulators of gene expression.

It has been determined that CTMP binds to PKB, such that the binding of CTMP to PKB inhibits PKB activity by affecting PKB phosphorylation. Thus, by modulating CTMP's ability to interact with PKB, it is possible to modulate the effects of PKB in general, such as in cell proliferation and insulin production.

Accordingly, there is provided a method for influencing the effect of CTMP on a cell comprising modulating the interaction of CTMP with other proteins, such as PKB. The yeast two hybrid system described in the Examples below can be used to identify additional binding partners of CTMP. Preferably, the method comprises bringing the cell into contact with an activator or an inhibitor of CTMP's ability to interact with other proteins, in particular PKB. Activators and inhibitors, which include CTMP mimics and are referred to collectively as modulators, may interact with CTMP by blocking PKB binding, or may interact with PKB, blocking CTMP binding. Still further modulators may influence the interaction of CTMP with PKB by targeting the factors and substrates that interact with CTMP or PKB, rather than CTMP itself.

The invention also provides a method of preventing or affecting an abnormality in a PKB signalling pathway, wherein the pathway involves an interaction between a CTMP protein and a CTMP binding partner, preferably PKB, comprising the step of disrupting or promoting said interaction. For example, the abnormality in the PKB pathway may have resulted in transformed cells and a CTMP modulator (e.g., CTMP or a modulator functioning as CTMP) may be used to reduce their proliferation or indeed reverse the effects of tranformation (see Example 11). CTMP modulators may also be used to study effects of insulin regulation.

In particular, a method is provided for treating a disease associated with an anomaly of PKB response or CTMP response comprising administering to a subject a pharmaceutically effective amount of a CTMP modulator. For example, the disease may be a disease associated with an anomaly in insulin regulation or be the uncontrolled proliferation of cells, i.e., cancer. CTMP modulators for use in such a method may be formulated according to conventional methodology, depending on the exact nature of the modulator, and will typically comprise the modulator or a precursor thereof in association with a biologically acceptable carrier.

In certain circumstances, the CTMP modulator may take the form of CTMP itself, such that exogenous CTMP is administered. Therapies may be designed to circumvent or overcome a CTMP gene defect or inadequate CTMP gene expression, and thus moderate and possibly prevent malignancy. In considering various therapies, however, it is understood that such therapies may be targeted to malignant tissues demonstrated to express mutant CTMP.

Delivery of the protein to the affected cells and tissues can be accomplished using appropriate packaging or administration systems. For example, CTMP may be formulated for therapeutic use with agents acceptable for pharmaceutical administration of proteinaceous agents and delivered to the subject by acceptable routes, such as via liposomes. Alternatively, small molecule analogs may be used and administered to act as CTMP agonists (or antagonists) and in this manner produce a desired physiological effect.

Moreover, CTMP or a modulator thereof may be provided to the cell in the form of a nucleic acid that can be translated in the cell to provide CTMP or a modulator thereof in situ. Thus, the invention includes methods of gene therapy comprising administering to a cell a nucleic acid encoding CTMP or a modulator thereof such that the nucleic acid is taken up by affected cells and expressed within the cell to produce CTMP or its modulator in sufficient amouts to provide effective function. The invention includes the administration of nucleic acids which possess a CTMP modulating activity per se, such as antisense oligonucleotides which target CTMP itself or a molecule which influences the activity of CTMP.

Transducing retroviral vectors can be used for somatic cell gene therapy especially because of their high efficiency of infection and stable integration and expression. The targeted cells must be able to divide and the expression level of normal protein should be high. The full length CTMP gene, or portions thereof, can be cloned into a retroviral vector and driven from its endogenous promoter or from the retroviral long terminal repeat or from a promoter specific for the target cell type of interest. Other viral vectors which can be used include adeno-associated virus, vaccinia virus, bovine papilloma virus, or a herpes virus such as Epstein-Barr virus. Gene transfer can also be achieved using non-viral methods, such as with liposomes, or using ex vivo methods. Cells produced by ex vivo methods can be injected serotologically into the targeted tissue(s).

In accordance with one aspect of the invention, a method is provided for suppressing the neoplastic phenotype of a cell comprising administering to the cell an agent selected from the group consisting of:
(a) a nucleotide sequence encoding CTMP protein;
(b) CTMP protein, fragments, polypeptides and derivatives of polypeptides;
(c) a polynucleotide strand antisense to a mutant CTMP gene;
(e) an agent to stabilize CTMP protein; and
(f) an agent to stabilize CTMP-PKB interaction.

Screening Assays

In a further aspect of the invention, screening methods are provided to identify potential modulators of CTMP activity. Typically, such a screen will comprise the steps of:
a) incubating a CTMP or fragment thereof, preferably CTMP, with the compound;
b) determining the compound-induced modulation in the activity of the CTMP, an alteration of the activity in the presence of the compound being indicative of a functional interaction between the compound and the CTMP.

In accordance with a further aspect of the invention, a method is provided for screening for an agent useful in treating a disorder characterized by an abnormality in a PKB signalling pathway, wherein the pathway involves an interaction between an CTMP protein and an CTMP binding partner, comprising screening potential agents for ability to disrupt or promote the interaction as an indication of a useful agent.

In accordance with a further aspect of the invention, a method is provided for identifying compounds modulating expression of a CTMP gene comprising contacting a cell with a candidate modulator wherein the cell includes a regulatory region of a CTMP gene operably joined to a coding region; and detecting a change in expression of the coding region.

CTMP may be used directly for binding studies and in the screening of possible modulators thereof. For binding studies, the polypeptide of the invention may be, for example, immobilised on a solid carrier like a microtiter plate or beads; or may bear one or more identifiable markers, like biotin or a radioactive, fluorescent or chemiluminescent group. In a preferred embodiment of the present invention, CTMP is used in a method for screening potential modulators of CTMP function. In such a method, the activity of CTMP is monitored by suitable means, for example by a functional assay which measures interaction with PKB, or PKB activity. Therefore, the invention provides a method for screening a compound which is a potential modulator of CTMP activity comprising the steps of:
a) incubating CTMP with the compound;
b) determining the compound-induced modulation in CTMP function, an alteration of the function in the presence of the compound being indicative of a functional interaction between the compound and CTMP.

Incubation conditions will vary according to the precise method used to detect the interaction between CTMP and the screened compound. In the case of transcription activation detection systems such as the yeast two-hybrid system, incubation conditions are suitable for gene transcription, such as those prevailing inside a living cell. Other detection systems, however, will require different incubation conditions. For example, if the detection of interaction is based on relative affinity in a chromatographic assay, for example as is known in affinity chromatography, conditions will be adjusted to promote binding and then gradually altered, such that the point at which the screened compound no longer binds to CTMP may be determined.

Incubation according to the invention may be achieved by a number of means, but the basic requirement is for CTMP or a fragment thereof and the screened compound to be able to come into contact with each other. This may be achieved by admixing CTMP or a fragment thereof and the compound, or by producing them in situ, such as by expression of nucleic acids encoding them. Where CTMP or the CTMP fragment and/or the compound are in the form of fusions with other polypeptides, they may be expressed as such in situ.

Thus, cell lines expressing CTMP may be cultured and a test compound added to the culture medium. After a period of incubation, CTMP activity can be determined and, optionally quantified to determine any changes that result from addition of the test compound. The effect of protein drugs/agents that interact with the CTMP's normal function can be studied in order to more precisely define the intracellular role of the protein. Therefore incubating cell cultures expressing CTMP with agents that affect CTMP-PKB interaction may help to elucidate the involvement of other proteins in PKB regulation.

The screening method of the invention can be based on a two-hybrid system. Such systems detect specific protein:protein interactions by exploiting transcriptional activators having separable DNA-binding and transcription activating domains, such as the yeast GAL4 activator, as illustrated below. If there is a specific interaction between CTMP or a fragment thereof and the compound, the DNA binding and transcription activating domains of the transcriptional activator will be brought into juxtaposition and transcription from the reporter gene will be activated.

Alternatively, the detection may be based on observed binding between CTMP or a fragment thereof, and the screened compound, or a fragment thereof. For example, the interaction between CTMP and a potential modulator may be assayed by monitoring the interaction of a portion of the modulator, known to be involved in modulation events, with CTMP.

CTMP or a fragment thereof may be used to screen for compounds which bind thereto by incubating it with the compound to be screened and subsequently "pulling down" CTMP complexes with an CTMP-specific antibody. Antibodies suitable for immunoprecipitation or immuno-affinity chromatography may be prepared according to conventional techniques, known to those of ordinary skill in the art, and may be monoclonal or polyclonal in nature. After the CTMP-compound complex has been isolated by affinity, the compound may be dissociated from the CTMP antibody and characterised by conventional techniques.

The interaction of CTMP or a fragment thereof with the screened compound may also be observed indirectly. For example, an inhibitor or activator of CTMP function may be detected by observing the effects of CTMP on PKB in the presence or absence of the compound. The function of CTMP or a fragment thereof may therefore be assessed by means of a kinase activity assay, employing a PKB kinase substrate in accordance with established assay procedures.

The screening system is preferably used to screen for compounds that are modulators of CTMP function, particularly where that function is related to PKB activity and cell proliferation. The system can be used to screen small molecule libraries, peptide libraries, phage display libraries, natural product libraries or screens based on the CTMP protein sequence can be designed.

In order to increase the understanding of CTMP activity and potentially improve CTMP modulators, isolated CTMP can be used to establish secondary and tertiary structure of the whole protein or at least of the areas responsible for the enzymatic activity and regulation. Conventional methods for the identification of the 3-dimensional structure are, for example, X-ray studies or NMR studies. The data obtained with these or comparable methods may be used directly or indirectly for the identification or improvement of modulators of CTMP. A commonly used method in this respect is, for example, computer aided drug design or molecular modelling. A further embodiment of the invention concerns the modulator identified with the polypeptide of the invention, or with the aid of the 3-dimensional structure derived therefrom, for use in a method of treatment.

Kits useful for screening such compounds may also be prepared in accordance with the invention, and will comprise essentially CTMP or a fragment thereof useful for screening, and instructions. Typically the CTMP polypeptide will be provided together with means for detecting an interaction between CTMP and the screened compound. Preferably, therefore, the screening kit comprises one of the detection systems set forth hereinbefore.

CTMP for use in kits according to the invention may be provided in the form of a protein, for example in solution, suspension or lyophilised, or in the form of a nucleic acid sequence permitting the production of CTMP or a fragment thereof in an expression system, optionally in situ. Preferably, the nucleic acid encoding CTMP or a fragment thereof encodes it in the form of a fusion protein, for example a GST fusion.

In a still further embodiment, the invention provides a compound that interacts directly or indirectly with CTMP or a fragment thereof, preferably a compound that modulates CTMP and/or PKB activity. Such a compound may be inorganic or organic, for example an antibiotic or antibody, and is preferably a proteinaceous compound involved in intracellular signalling.

Compounds according to the invention may be identified by screening using the techniques described hereinbefore, and prepared by extraction from natural sources according to established procedures, or by synthesis, especially in the case of low molecular weight chemical compounds. Proteinaceous compounds may be prepared by expression in recombinant expression systems, for example a baculovirus system, or in a bacterial system. Proteinaceous compounds are mainly useful for research into the function of signalling pathways, although they may have a therapeutic application.

Low molecular weight compounds, on the other hand, are preferably produced by chemical synthesis according to established procedures. They are primarily indicated as therapeutic agents. Low molecular weight compounds and organic compounds in general may be useful as antiproliferative agents, for use in the treatment of a condition associated with cell growth, or for treating diabetes.

Animal Models

The present invention also provides for the production of transgenic non-human animal models for the study of the CTMP tumour suppressor gene function, to study the mechanisms of carcinogenesis as related to the CTMP gene, to study the PKB signaling pathway, for the screening of candidate pharmaceutical compounds, for the creation of explanted mammalian cell cultures which express the protein or mutant protein or in which the CTMP gene has been inactivated by knock-out deletion, and for the evaluation of potential therapeutic interventions.

Animal species which are suitable for use in the animal models of the present invention include, but are not limited to, rats, mice, hamsters, guinea pigs, rabbits, dogs, cats, goats, sheep, pigs, and non-human primates such as monkeys and chimpanzees. For initial studies, transgenic mice and rats are highly desirable due to their relative ease of maintenance and shorter life spans. For certain studies, transgenic yeast or invertebrates may be suitable and preferred because they allow for rapid screening and provide for much easier handling. For longer term studies, non-human primates may be desired.

There are several ways in which to create an animal model for CTMP studies. Generation of a specific mutation in a homologous animal gene is one strategy. Secondly, a wild type human gene and/or a humanized animal gene could be inserted by homologous recombination. Thirdly, it is also possible to insert a mutant (single or multiple) human gene as genomic or minigene cDNA constructs using wild type or mutant or artificial promoter elements. Fourthly, knock-out of the endogenous homologous animal genes may be accomplished by the insertion of artificially modified fragments of the endogenous gene by homologous recombination. The modifications include insertion of mutant stop codons, the deletion of DNA sequences, or the inclusion of recombination elements (lox p sites) recognized by enzymes such as Cre recombinase.

To inactivate the CTMP gene chemical or x-ray mutagenesis of mouse gametes, followed by fertilization, can be applied. Heterozygous offspring can then be identified by Southern blotting to demonstrate loss of one allele by dosage, or failure to inherit one parental allele using RFLP markers.

To create a transgenic mouse, which is preferred, CTMP (or a mutant version) can be inserted into a mouse germ line using standard techniques of oocyte microinjection or transfection or microinjection into embryonic stem cells. Alternatively, if it is desired to inactivate or replace the endogenous CTMP gene, homologous recombination using embryonic stem cells may be applied. In general, techniques of generating transgenic animals are widely accepted and practiced. A laboratory manual on the manipulation of the mouse embryo, for example, is available detailing standard laboratory techniques for the production of transgenic mice (Hogan et al., 1986).

The invention is further described, for the purposes of illustration only, in the following examples.

EXAMPLES

The examples are described for the purposes of illustration and are not intended to limit the scope of the invention.

Methods of molecular genetics, protein and peptide biochemistry and immunology referred to but not explicitly described in this disclosure and examples are reported in the scientific literature and are well known to those skilled in the art. For example, standard methods in genetic engineering such as random priming, subcloning, sequencing, cleavage with restriction enzymes, gel purification, ligation, transformation and annealing are carried out essentially as described in Sambrook et al., Molecular Cloning: A laboratory manual, 2nd Ed., Cold Spring Harbor Laboratory Press, Cold Spring Harbor N.Y., 1989.

Example 1

Identification of Human CTMP

CTMP was initially identified as a potential PKB-interacting protein using the yeast two-hybrid system (Fields and Song, 1989, Nature, 340, 245-246) to screen a HeLa cDNA library. This cell line was shown to express PKB alpha (Coffer and Woodgett, 1991, Eur. J. Biochem., 201, 475-481). We used as a bait the kinase catalytic domain plus the C-terminal regulatory domain of the alpha isoform (pGBT-KIN-CT). The construction of the yeast vectors is described below.

Yeast vectors. Yeast vector plasmids containing the Gal4 DNA binding domain (amino acids 1-147, pGBT9) and the Gal4 activation domain (amino acids 768-881, pGAD424) as well as the control plasmids pCL1 (full-length Gal4 gene), pVA3 (p53 gene), pTD1 (SV40 large T antigen), and pLAM5' (human Lamin C gene) are available commercially (Clontech, Palo Alto, Calif.). pGBT-PH127 and pGBT-PH150 encoding in-frame fusions of amino-acids 1-127 or 1-150 of human PKB alpha respectively, are constructed by cloning PCR fragments generated with specific primers into the EcoRI and BamHI sites of pGBT9. BamHI-EcoRI PCR fragments encoding amino-acids 1-411 (PH-KIN), 1-480 (PH-KIN-CT), 147-480 (KIN-CT), 147-411 (KIN) and 411-480 (CT) are first cloned in the corresponding site of pGex2T (available commercially, AP-Biotech) in-frame fusions with GST, then subcloned in the pPC62 vector containing the Gal4 DNA binding domain (a gift from Dr D. Nathans, Howard Hughes Medical Institute, Baltimore, Md.), using PstI-BamHI and EcoRI-XbaI adapters. The XhoI-XbaI fragments are then subcloned in the XhoI-EcoRI sites of pGBT9 using an XbaI-EcoRI adapter, resulting in pGBT-PH-KIN, pGBT-PH-KIN-CT, pGBT-KIN-CT, pGBT-KIN and pGBT-CT, respectively, resulting in-frame fusions with the GAL4 DNA binding domain.

The yeast vectors are used for library screening in the commercially available yeast strain, HF7c, (MATa, ura3-52, his3-200, lys2-801, ade2-101, trp1-901, leu2-3, 112, gal4-542, gal80-538, LYS2::GAL1-HIS3, URA3::(GAL4 17-mer)3-CYC1-lacZ; Clontech, Palo Alto, Calif.) in the MATCHMAKER Two-Hybrid System (Clontech, Palo Alto, Calif.). In HF7c, HIS3 is fused to a GAL1 promoter sequence and LacZ is fused to three copies of a 17-mer GAL4 consensus sequence plus the TATA sequence of the CYC1 promoter. Both HIS3 and LacZ are responsive to GAL4 activation. Yeast techniques including transformation are performed according to the instructions in the MATCHMAKER Two Hybrid System and as described (Ausubel, et al. (1994) Current Protocols in Molecular Biology, John Wiley and Sons, New York, N.Y.).

To determine if PKB's kinase domain with its carboxyl-terminal extension could interact with other proteins, it was fused to the GAL4 DNA binding domain and a HeLa cDNA library fused to the GAL4 transcriptional activation domain in the yeast reporter strain HF7c was screened. Briefly, pGBT-KIN-CT is transformed into HF7c with and without the control plasmids (pGAD424, pCL1 or pTD1). Colonies from this transformation are tested for HIS3 and LacZ expression to confirm that the kinase domain plus the C-terminal regulatory domain alone does not activate transcription within the test system. The HF7c strain transformed with pGBT-KIN-CT alone is then further transformed with sufficient HeLa S3 cDNA library (commercially available) inserted into the two-hybrid activation vector pGADGH to produce $1.5 \times 10^6$ yeast Leu$^+$/Trp$^+$ transformants. Doubly transformed cells are plated onto Leu$^-$, Trp$^-$, His$^-$ (triple minus) plates and incubated at 30° C. for 3-8 days. Positive colonies are picked, restreaked onto triple minus plates and assayed for LacZ activity by the filter assay. Library clones that are His+ and LacZ+ are then cured of the pGBT-KIN-CT plasmid and tested again for His auxotrophy and LacZ activity. Cured clones that are negative in both assays are then mated to transformants of PCY2 (Chevrey and Nathans, 1992, Proc. Natl. Acad. Sci. USA, 89, 5789-5793) containing either pGBT9, pGBT-KIN-CT, pLAM5' or pTD1. The clones corresponding to the diploids that became positive for His auxotrophy and LacZ activity only in the presence of pGBT-KIN-CT are chosen for sequencing.

In $1.5 \times 10^6$ primary transformants screened, 7 positive clones were identified. This clone (pGADGH.CTMP) specifically interacts with PKB as determined by activation of the reporters for His auxotrophy and lacZ activity in the yeast two hybrid system in the yeast strain, SFY526. In fact, the interaction is seen only in the constructs that contain the C-terminal regulatory domain, namely, pGBT-PH-KIN-CT (full-length PKB), pGBT-KIN-CT deltaPH), and pGBT-CT, supporting a specific interaction of the product of this clone with the C-terminal regulatory domain of PKB. Moreover, the three constructs containing the C-terminal regulatory domain do not interact with unrelated proteins such as the tumour suppressor, p53, or the human Lamin C. Interestingly, the C-terminal domain of PKB is phosphorylated in response to insulin activation, suggesting a role for CTMP as a modulator of insulin action. All seven positive clones contain a cDNA insert of 1.3 Kb in length.

The cDNA is sequenced using SEQUENASE.TM.2.0 Kit (US Biochemicals) and the resulting sequence is shown in (SEQ ID NO:1). Surprisingly, the cDNA contains an ALU sequence repeat of ~300 nt at its 3' end. Searches of the nucleotide databases using the cDNA sequence without the ALU repeat, identified four different types of human expressed sequence tags (ESTs; Nos. W76206, AA045430, F00707 and AA526313) as displaying similarity to the cDNA sequence (FIG. 1B, type I to IV). The EST clones were sequenced and the sequences shown to correspond to nucleotides 211-769, 308-983, 95-331 and 144-331, respectively, of the full length cDNA sequence. Type I is homologous to part of the cDNA and has a long 5' UTR sequence including a polyadenylation consensus sequence. Like Type I, Type II EST is homologous to part of the cDNA coding sequence, but it does not contain an ALU repeat and therefore contains a divergent 5' UTR. Type III and IV ESTs are homologous to part of the cDNA only until nucleotide 331. Both types present divergent sequences that introduce a stop codon immediately after the divergent point, possibly resulting in the production in both cases of a truncated protein, although prior to the present invention no such protein product was known to exist.

Based on a search of the NCBI Database of CONTIGs with the nucleic acid sequence, the CTMP gene was determined to be localized on chromosome 1, and to have 6 encoding exons and 5 introns. A pseudogene on chromosome 15 was also identified.

The cDNA encodes a 240 amino acid protein (SEQ ID NO:2) that we have termed C-Terminal Modulator Protein (CTMP). Searches in protein databases (PIR, Swiss-Prot, SP-TREMBL and Structure database), revealed no significant homologies of the CTMP protein with known proteins or protein domains, other than to a portion of CTBP, a protein previously identified in the laboratories of the present inventor. CTMP may therefore represent the prototypical member of a new family of proteins.

Although this example describes the human CTMP amino acid sequence, it will be apparent to one of ordinary skill in the art that related proteins and peptides can be easily prepared using degenerate or mutated oligonucleotides to amplify related nucleotide seqeunces from biological samples or by peptide synthesis.

Example 2

Expression of CTMP in Human Tissues

Human tissue samples are analyzed for the presence of the CTMP transcript by reverse transcriptase-polymerase chain reaction (RT-PCR) to determine CTMP expression levels in various human tissues. The following tissues are tested: Brain, heart, kidney, liver, lung, trachea, mammary gland, prostate, skeletal muscle, testis and uterus.

Human RNA samples are purchased from Clontech with the exception of HeLa cell RNA that is prepared with the Trizol protocol (GIBCO). RT-PCR reactions are performed using the GeneAmp RNA PCR Kit (Perkin Elmer). Briefly, 1 µg samples of total RNA obtained from various human tissues is reverse transcribed in a total volume of 20 µl with 2.5 U/µl of MuLV, 1 U/µl of Rnasin, 1 mM of dNTPs, 2.5 µM of Oligo d(T), 5 mM of MgCl$_2$ and $10^5$ copies of synthetic pAW109 control RNA, essentially as described in the GeneAmp RNA PCR kit protocol (Perkin Elmer). The particular conditions used are 15 minutes at 25° C., followed by 60 minutes at 42° C. Enzymes are inactivated for 5 minutes at 90° C. Standard PCR reactions are then carried out with the Taq polymerase in a total volume of 20 microlitres using as a template 5 microlitres of the previously transcribed RNA. Specific primers for human CTMP cDNA 28913(5' TCTGAGGAAGTCATTCT-TAA G-3'; SEQ ID NO:3)/28918(5' CTCATCAACACTCT-GAACATT; SEQ ID NO:4) or for IL-1α DM151 (5' GTCTCTGAATCAGAAATCCTTCTATC; SEQ ID NO:5) and DM152 (5' CATGTCAAATTTCACTGCTTCATCC-3'; SEQ ID NO:6) are used in the reactions for amplification of respectively a 545 bp or a 308 bp band. DM151/DM152 are used to quantify the efficiency of the reverse transcription step. They amplify the IL-1α specific sequence present in the synthetic pAW109 RNA added in all the reverse transcription reactions, but also the endogenous IL-1α transcript in the tissues expressing it at a size of 421 bp. For positive control, 5 ng of pBLM.CTMP vector containing the human CTMP cDNA is used.

As expected, the 545 bp band is correctly amplified in the two controls of CTMP cDNA and RNA from HeLa cells. The CTMP gene is expressed at higher levels in skeletal muscle, testis, uterus, brain and kidney; moderately expressed in trachea, mammary gland and prostate; and only poorly or not expressed in heart, liver and lung. Surprisingly, two larger products of ~600 and ~700 bp are also amplified in all tissue samples giving an amplified 545 bp product, with the exception of uterus and Hela cells, a cervix carcinoma cell line. Sequencing of both the larger products after gel purification revealed an insertion between nucleotides 331 and 332 of a stretch of DNA homologous to the sequences found in ESTs type III for the ~600 bp product, and type IV for the ~700 bp product. It is therefore apparent that the CTMP gene can produce at least three different variants that may be differentially regulated.

Example 3

Expression of CTMP in Bacteria

The bacterial strain BL21 (DE3)pLysS (commercially available) is used for the production of (HIS)6-tagged CTMP. For the in vitro characterisation of CTMP, the human cDNA is isolated from pCTMP (a plasmid encoding CTMP derived from Example 1) and BamHI and EcoRI restriction sites introduced by PCR to introduce the fragment into the Bam HI-EcoRI digested pET28a (Groves et al., Cell 96, 99-110). Protein is expressed essentially as described by Groves et al. and is purified by means of the HIS6 tag.

Example 4

Expression of CTMP in Eukaryotic Cells

For the detection of overexpressed human CTMP, a rabbit antiserum is raised against a synthetic peptide, derived from the predicted human CTMP amino acid sequence (SEQ ID NO:2), which is conjugated to keyhole limpet haemocyanin as described in Pix et al., J. Biol. Chem. (1993), 268, 7330-7337 or against the bacterially expressed and purified His$_6$-CTMP described above, for example. Antibody titer is tested (Pix et al., J. Biol. Chem. (1993), 7330-7337) on Western blots of lysates of E. coli expressing recombinant CTMP (from Example 3). Peptide-specific antibodies are purified on columns of protein A-Sepharose@ (Pharmacia) followed by Affi-Gel 10® (Bio-Rad) to which the immunogenic peptide (or CTMP) has been coupled following the manufacturer's recommendations. Antibodies are eluted with 50 mM Tris-HCl, pH 7.4 containing 6 M urea, and dialysed extensively against PBS.

COS-1 cells (ATCC CRL 1650) are maintained in DMEM supplemented with 10% FCS at 37° C. For transfection, cells are incubated in DMEM containing 0.7 µg/ml plasmid DNA, pCTMP and 7 µl/ml Lipofectin® (Gibco BRL). After 5 h, an equal volume of DMEM/20% FCS is added. The transfection is terminated 12 h later by replacing the medium with fresh DMEM/10% FCS, or by passaging the cells onto glass coverslips (for immunolocalisation). Protein expression is analysed 24 h later via immunoblotting.

Immunoblotting is carried out as described in Pix et al., J. Biol. Chem. (1993), 268, 7330-7337, using the antibody at a dilution of 1:20. The primary antibody is detected using an ECL kit® (Amersham).

The transfection of the human cDNA into COS-1 cells leads to the appearance of a CTMP-immunoreactive polypeptide on Western blots of whole-cell lysates. This species is normally observed only at very low levels in lysates from cells transfected with control vector alone.

Protein levels of CTMP are also analysed in several cell lines using an antibody specific to human CTMP. Endogenous CTMP is detected in extracts from HeLa and HEK293 cells, with weaker expression found in COS-1 cells. This data is in agreement with the observation of CTMP RNA transcripts in kidney extracts detected by RT-PCR. Weaker CTMP expression is seen in the human SJRH30 rhabdomyosarcoma cell line, and no signal is detected in the rat H9C2 myocardium cell line under the experimental conditions used. As is apparent to one of ordinary skill in the art, conditions can be altered to increase sensitivity of detection if desired.

Example 5

Analysis of the Subcellular Localisation of GFP-CTMP Fusion Protein

A GFP-CTMP fusion protein is expressed in NIH3T3 cells and examined by confocal microscopy to assess the subcellular localisation of CTMP. CTMP is determined to be localized to the leading edge of membrane ruffles.

The GFP-CTMP expression vector is prepared as described briefly below. The 1.3 Kb SmaI-XhoI insert of pGADGH.CTMP (Example 1) is subcloned into the corresponding sites of pBluescript.M13-(KS, available commercially) to give the vector pCTMP. The vector pGFP.CTMP$_s$ is generated by PCR cloning into the BamHI site of pEGFP.C1 (Clontech). CTMP$_s$ refers to a CTMP protein starting at the natural ATG of the cDNA.

The cellular localization of CTMP is investigated by confocal microscopy. The GFP-CTMP fusion protein is expressed in NIH3T3 cells, one of many cell lines suitable for this analysis. Briefly, NIH3T3 cells are seeded in 6 wells cluster containing a 1 cm diameter glass coverslip and maintened in DMEM supplemented with 10% calf serum. Cells are transfected by the BBS calcium phosphate technique (Chen and Okayama, 1987, Mol. Cell Biol., 7, 2745-2752) in the 6 well clusters with 5 microgrammes of total DNA. At 18 hours after transfection, the cells are washed twice with serum-free medium and incubated 24 hours in DMEM containing 0.5% calf serum (CS). The coverslips are mounted and observed at 37° C. as described in Fischer et al. (1998, Neuron, 20, 847-854) in a purpose-built observation chamber (Life Imaging Services, Olten, Switzerland) using a GFP-optimized filter set (Chroma Technologies, Battleboro, Vt.). Illumination density is adjusted using neutral density filters and images are taken with a MicroMax cooled CCD camera (Princeton Instruments, Trenton, N.J.) and Metamorph 3.0 imaging software (Universal Imaging Corporation, West Chester, Pa.).

In contrast to GFP (control protein), which is expressed in all compartments of the cell, the fluorescent GFP-CTMP fusion protein is visualized in structures resembling membrane ruffles, highly dynamic structures of the plasma membrane (Ridley, 1994, Nature, 382, 325-331). We can therefore infer that CTMP is responsible for the membrane-associated localization of GFP-CTMP. As membrane ruffling has been observed at the leading edge of motile cells, for example, when cells migrate in response to chemoattractants, a time-lapse cine-microscopy of NIH-3T3 cells expressing GFP-CTMP is carried out. Pictures are taken every 5 seconds with cell motion clearly visible at 30, 60 and 90 seconds. The time-lapse cine-microscopy showed the fusion protein at the leading edge of the moving cells in structures resembling membrane ruffles. Membrane ruffling reflects the active process of actin reorganization and localization of CTMP to membrane ruffles.

To further confirm the membrane localization of CTMP, fractionation of HeLa cells into cytosolic (S100) and membrane (P100) fractions is performed. CTMP is exclusively detected in the P100 fraction. Furthermore, analysis of the CTMP protein sequence reveals the presence of a putative trans-membrane domain corresponding to amino acids Ile156 to Thr177.

Example 6

CTMP Homodimerizes In Vivo

PDZ domains were first described as modules able to bind the extreme C-termini of target proteins due to the presence of a GLGF motif (Pontig et al., 1997, Bioessays, 19, 469-479). It is now established that PDZ domains also allow homo and heterodimerization (Oschkinat, 1999, Nat. Struct. Biol., 6, 408-410; Tochio et al., 1999, Nat. Struct. Biol., 6, 417-421; Hillier et al., 1999, Science, 284, 812-815; Xu et al., 1998, EMBO J., 18, 1309-1320). Interestingly, CTMP contains a GLGF motif suggesting that it may contain a PDZ motif.

The ability of CTMP to homo-dimerize in COS-1 cells is tested using a eukaryotic GST pull-down assay (Chatton et al., 1995, Biotechniques, 18, 142-145). A "Flag" (F) epitope tagged-CTMP expression vector and a GST-CTMP expression vector are prepared as follows. The vector pCTMP (Example 5) is used to prepare the vectors PF.CTMP$_L$, pF.CTMP$_s$, and pF.CTMPΔN1, generated by PCR cloning into the BamHI sites of the respective pSG5.FlagNt-Puro vectors (available commercially from Stratagene and modified to contain a Flag epitope and puromycin selection marker). The pSG5.FlagNt-Puro vectors allow the introduction of a Flag epitope tag (F) into the amino terminus of the encoded protein. CTMP$_L$ corresponds to the protein found in the Gal4-AD-CTMP fusion protein recovered from the yeast screen (Example 1), where the 5' untranslated region (UTR) codes for an additional 15 amino acids at the N-terminus of the protein and is identical to wild-type CTMP in terms of PKBα binding and inhibition. CTMP$_s$ is a CTMP protein starting at the natural ATG of the cDNA. pGST.CTMP$_s$ and pGST.CTMPdeltaC1/deltaC2 are created by PCR cloning in the NdeI-EcoRI or the NdeI-BamHI sites of the pBC vector, respectively (Chatton et al., 1996; Stratagene).

COS-1 cells are maintained in DMEM supplemented with 10% fetal calf serum (FCS, Life Technologies). COS-1 cells are co-transfected with the expression vectors pF.CTMPs (2.5 µg) and either pGST (2.5 µg) or pGST-CTMPs (2.5 µg), by the BBS calcium phosphate technique (Chen and Okayama, 1987) essentially as described in Example 5, other than 0.5% fetal calf serum (FCS) is used instead of 0.5% calf serum medium. The effect of stimulation by pervanadate is studied by inclusion of 0.1 mM pervanadate prepared in 0.2 mM H$_2$O$_2$ (Posner et al., 1994, J. Biol. Chem., 269, 4596-4604) in the medium for 15 minutes, and comparing to control cells grown in the absence of pervanadate.

A modified version of the eukaryotic GST pull-down assay (Chatton et al., 1995) is used to detect protein-protein interactions. Briefly, transfected COS-1 cells are lysed in 200 µl of lysis buffer A (50 mM Tris pH 7.8, NaCl 120 mM, NP40 1%, NaF 25 mM, βGlycerol-phosphate 40 mM, NaVO$_3$ 0.1 µM, Mycrocystin LR 1 µM, PMSF 1 mM, Benzamidine 1 mM). Cell lysates are cleared by centrifugation (5 min at 10000 g) and 180 µl aliquots are incubated for 2 hours at 4° C. in 1 ml of either Low (50 mM Tris-HCl, pH 7.8, 250 mM NaCl and 0.1% NP40), Medium (50 mM Tris-HCl, pH 7.8, 1 M NaCl and 0.5% NP40) or High (SDS 0.5%, NP40 0.5% and Na-Deoxycholate 0.1% in PBS, RIPA Buffer) stringency buffer with 40 µl of glutathione-sepharose beads (50% suspension, Sigma chemicals). The beads are then washed three times with the same buffer used for the binding, and finally re-suspended in 40 µl of 2× SDS-PAGE loading buffer. The remaining 20 µl are used to check the expression level of the protein.

Proteins are fractionated by SDS-PAGE, transferred to PVDF (Immobilon-P) membranes (Millipore) and analyzed by immuno-blotting. After 1 hour of saturation in PBSTM (PBS plus 0.1% Tween-20 (Bio-Rad) and 3% skimmed milk powder (Fluka), the membranes are incubated either overnight at 40° C. or for 2 hours at room temperature with specific primary antibodies in PBSTM (0.3% milk). Anti-Flag (Eastman Kodak) and anti-GST polyclonal antibody are used at a dilution of 1/2000 and 1/500, respectively. The membranes are then washed three times with PBST (no milk) and then incubated for 1 hour at room temperature with secondary antibodies coupled to either peroxidase or alkaline phosphatase (diluted 1/10000) in PBSTM (0.3% milk). Secondary antibodies are commercially available (Amersham: anti-mouse and anti-rabbit horseradish peroxidase conjugated; Sigma: anti-rabbit alkaline phosphatase conjugated; and Southern Biotechnology Associates: anti-mouse alkaline phosphatase conjugated. The membranes are finally washed three times as above before revealing signal with the ECL detection kit (Amersham) or the alkaline phosphatase detection kit (Bio-Rad), respectively.

CTMP is specifically retained on GST-CTMP beads and the interaction is very stable since it still occurrs in high salt buffer or high detergent buffer (RIPA buffer). The interaction also still occurs if the cells are stimulated with pervanadate, a potent activator of PKB.

Deletion mutants of CTMP are used to localize the interaction domain of CTMP in dimerization. COS-1 cells are co-transfected essentially as described above with the expression vectors pF.CTMPs (2.5 µg) or pF.CTMPΔN1 (2.5 µg) with either pGST (2.5 µg of pGST), pGST-CTMPs (2.5 µg), pGST-CTMPΔC1 (2.5 µg) or pGST-CTMPΔC2 (2.5 µg). GST pull-down assays are performed at medium stringency as described above. Full-length CTMP is not retained on the GST-C-terminal deletion mutant ΔC1 and ΔC2, in contrast to ΔN1 that is strongly retained most notably by GST-ΔC2 rather than ΔC1 or full length CTMP. These data strongly suggest that the C-terminal portion of CTMP containing the GLGF motif has a high affinity for the N-terminal part of the protein and demonstrates that CTMP is able to dimerize in-vivo. It is also proposed that the GLGF binding groove of a CTMP dimer may recruit the last amino acids of PKB as a peptide recognition motif.

Example 7

CTMP Interacts with PKB at the Plasma Membrane in Mammalian Cells

CTMP was initially identified as a potential PKB-interacting protein in a yeast system. This example describes the characterization of the PKB-CTMP interaction in vivo, establishing a PKB-CTMP interaction in human cells. The PKBα-CTMP interaction is shown to occur in mammalian cells by co-immunoprecipitation of the two proteins. Briefly, the expression vectors, pHA-PKBα (7.5 µg; namely pCMV5-HA-PKBα), pHA-m/p-PKBα (7.5 µg; namely pCMV5-HA-m/p-PKBα) (both described by Andjelkovic et al., 1997) or a PKB C-terminal GST fusion, pGST-PKBCter, are used to transfect COS-1 cells. pGST-PKBCter is created by cloning of an NdeI-EcoRI PCR fragment of pCMV5.HA.PKBα into the corresponding sites of the pBC vector (Chafton et al., 1995).

COS-1 cells are maintained in DMEM supplemented with 10% fetal calf serum (FCS, Life Technologies) and are transfected in culture dishes (90 mm) essentially as described in Example 6, but using 15 µg of total DNA.

To demonstrate that immuno-precipitated CTMP can pull-down PKBα in the P100 fraction, COS-1 cells are transfected with expression vectors encoding F.CTMPs (7.5 µg of pF.CTMPs, see Example 6) and HA-PKBα (7.5 µg of pCMV5-HA-PKBα). After stimulation with pervanadate (0.1 mM for 15 min), the cells are lysed and fractionated as described below for co-immunoprecipitation with the anti-Flag antibody. Expressed proteins are revealed with anti-HA and anti Flag monoclonal antibodies and CTMP interacting proteins are revealed with the anti-HA.

To demonstrate that immuno-precipitated CTMP can pull-down the C-terminal regulatory domain of PKB in the cytosolic fraction, COS-1 cells are transfected with expression vectors encoding F.CTMPs (7.5 µg of pF.CTMPs) and either GST (7.5 µg of pGST) or GST-PKB$_{Cter}$ (7.5 µg of pGST- PKBCter). Fractionation and immuno-precipitation are performed as described below. Expressed proteins are revealed with an anti-Flag monoclonal antibody and an anti-GST polyclonal antibody (see Example 6) and CTMP interacting proteins are revealed with the anti-GST polyclonal antibody (see Example 6).

Transfected cells are lysed in high detergent (NP40, 1%) lysis buffer to prepare a total cell extract. Under these conditions, the C-terminal regulatory domain deletion mutant protein (GST-PKBCter) is detected complexed to immuno-precipitated CTMP, but the full-length PKBα protein is not co-immunoprecipitated. To test whether the interaction between CTMP and PKBα is promoted by intact plasma membrane structures, transfected COS-1 cells are lysed in a Hepes-Sucrose based buffer that, in contrast to NP40-based lysis buffer, allows the preparation of cytosolic (S100) and intact membrane (P100) fractions for immuno-precipitation.

Briefly, transfected COS-1 cells are scraped in 450 μl of HES buffer (20 mM Hepes pH 7.4, 1 mM EDTA, 250 mM Sucrose, NaF 25 mM, bGlycerol-phosphate 40 mM, NaVO$_3$ 0.1 μM, Mycrocystin LR 1 μM, PMSF 1 mM, Benzamidine 1 mM) and lysed by drawing through a 25 Gauge needle 15 times. Nuclei are removed by centrifugation for 10 min at 1000 g at 4° C. Additional centrifugation of the supernatant at 100000 g for 30 min at 4° C. results in the preparation of the P100 (pellet) and S100 (supernatant) fractions. P100 fractions are re-suspended in HES buffer containing 0.1% NP40, and incubated on ice for 1 hour prior to removal of insoluble material by centrifugation (5 min at 10000 g). 200 μg of either fraction are incubated with 5 μg of anti-Flag antibody (Sigma chemicals) and 800 μl of Low stringency buffer (see Example 6) for 2 hours at 4° C., followed by 2 hours at 40° C. with 40 μl of protein A/protein G-sepharose mix (1:1 ratio by volume) (AP Biotech, as a 50% suspension). After two washes with Low stringency buffer and one with Medium stringency buffer, the beads are re-suspended in 40 ml of 2× SDS-PAGE loading buffer. Proteins are fractionated by SDS-PAGE, transferred to nitrocellulose membranes and analyzed by immuno-blotting. Proteins are detected by Western-blot essentially as described above in Example 6 using the anti-HA 12CA5 Mab diluted 1/500 (for HA.PKB) or anti-GST (for GST.PKBCter).

The efficiency of the fractionation procedure can be judged by detecting transfected m/p-PKB, a PKB protein containing a myristylation/palmitoylation site for constitutive anchoring to the membrane using anti HA antibody. After fractionation, m/p-PKBα is found to be exclusively in the P100 pellet, as expected. In contrast, under the conditions used, PKBα is present in both S100 and P100 fractions. However, PKBα is detected together with immuno-precipitated CTMP only in the P100 fraction. Stimulation of COS-1 cells by vanadate (as described above) strongly reduces the PKBα-CTMP interaction. In addition, the GST-PKBCter fusion protein can also be found complexed to CTMP in the cytosolic fraction.

Therefore, in starved COS cells, i.e when PKB is inactive, CTMP interacts with full-length PKB, preferably when both proteins are localized on the plasma membrane. The interaction is greatly reduced when the cells are stimulated with pervanadate i.e. when PKB is catalyticaly active. Although PKB lacks ability to interact with CTMP in the cytosolic fraction, the GST-PKBCter deletion mutant does interact with CTMP in the cytosolic fraction. Without wishing to be bound by theory, the present inventors propose that PKB's PH and/or Catalytic domains has a strong inhibitory effect on the C-terminus regulatory domain binding properties when PKBα is not bound to the membrane. The PH domain of PKB may impede CTMP because it can also interact in cis or trans with the catalytic or the C-terminal regulatory domain when not tethered to the membrane, and therefore creating a closed conformation inaccessible to cytosolic CTMP.

Example 8

Post-Translational Modification of CTMP

To explore a potential mechanism for the inhibitory effect of pervanadate on PKBα-CTMP complexes, phosphorylation of CTMP was examined during PKB activation. For in vivo labelling, cells were starved for 15 hours in DMEM without serum or phosphate, and then incubated for 4 hours in this medium containing 1 mCi of $^{32}$P-orthophosphate. Cells were then lysed, and FLAG-CTMP immuno-precipitated as described above. In vivo labelling of cells stably expressing Flag-CTMP with $^{32}$P-orthophosphate demonstrated an approximately 4-fold increase in CTMP phosphorylation after pervanadate treatment, suggesting that CTMP is regulated at the post-translational level.

In vitro studies were carried out to establish which serine or threonine residues of CTMP could be phosphorylated. Myc-PDK1 was used to phosphorylate His6CTMP in Cos cells. The resulting phosphorylated CTMP was immunoprecipitated with 9E10 antibody (specific for the His tag) and subjected to mass spectrophotometric (MS) analysis and phosphopeptide mapping. The results demonstrate phosphorylation of the peptide SFSSEEVILK (Ser-35 through Lys-44) and SLT (Ser-238 to Thr-240). The phosphorylation sites were identified as Ser-35 and Ser-238, and to a lesser extent Ser-37, suggesting these sites as potential in vivo phosphorylation sites.

Example 9

CTMP Modulation of PKB Activity

This example addresses whether the interaction of CTMP with PKB results in the modulation of PKB catalytic activity. PKB is a Ser/Thr protein kinase that needs to be phosphorylated on two residues, Thr 308 in the activation loop and Ser 473 in the C-terminal regulatory domain, to be fully active. This activation is achieved when cells are stimulated with various factors, such as insulin or an insulino-mimetic chemical compound such as pervanadate. To test the influence of CTMP on PKB kinase activity, immune complex kinase assays are carried out on whole cell extract from transfected COS cells stimulated with pervanadate.

COS-1 cells are transfected with expression vectors for PKBα (2.5 μg of pHA.PKB) and with CTMPs (1,25; 2.5; 5 or 10 μg of pF.CTMPs). After stimulation with 0.1 mM pervanadate for 10 minutes, immune kinase assays are performed in duplicate. Briefly, transfected COS-1 cells are lysed on plates with 450 μl of Lysis Buffer A (50 mM Tris pH 7.8, 120 mM NaCl, 1% NP-40, 25 mM NaF, 40 mM beta-glycerophosphate, 0.1 microM NaVO$_3$, 1 μM Mycrocystin LR, 1 mM PMSF, 1 mM benzamidine). Lysates are cleared by centrifugation (5 min at 10 000 g), and HA epitope-tagged PKB protein immuno-precipitated from 200 mg of cell extracts, with the anti-HA MAb 12CA5 coupled to protein A Sepharose beads (AP Biotech). The immune complexes on beads are washed once with Lysis buffer A containing 0.5 M NaCl, once with Lysis buffer A and once with 50 mM Tris-HCl (pH 7.8), 1 mM PMSF and 1 mM benzamidine. In-vitro kinase assays are performed for 30 min at 30° C. in a 50 μl of reaction mixture (50 mM Tris-HCl, pH 7.8; 1 mM PMSF and 1 mM benzamidine; 10 nM okadaic acid (LC laboratories);

0.1% (vol/vol) 2-mercapto-ethanol; 10 mM $MgCl_2$; 1 μM protein kinase A inhibitor peptide (Bachem); 50 μM [γ-$^{32}$P] ATP (1000 to 2000 cpm/pmol, Amersham) and 30 mM peptide GRPRTSSAEG as PKB substrate (Cross et al., 1995). Activity is determined as described by Alessi et al. (1996). In the presence of increasing amounts of expressed CTMP, PKB becomes less active than in the absence of CTMP, indicating an inhibitory effect of CTMP on PKB kinase activity.

The phosphorylation status of PKB can be determined by Western-blot using phospho-specific antibodies directed against phosphorylated Thr 308 and Ser 473 residues. Mouse monoclonal or rabbit polyclonal anti-phospho Ser 473 (New England Biolabs), rabbit polyclonal anti-phospho Thr 308 (New England Biolabs) and anti-PKB PAb10 (Jones et al, 1991) can be used as specific primary antibodies respectively at dilution 1/1000, 1/1000 and 1/500. To avoid confusion with endogenous PKB, the Western blot procedure is carried out using immuno-precipitated HA-PKBα. Expressed PKBα and CTMP proteins are detected with the anti-HA and anti-Flag monoclonal antibodies. CTMP expression leads to a reduction of phosphorylation on both residues but most notably on the S473 site, suggesting that CTMP may impede PKB activation by blocking S473 phosphorylation due to an as yet unidentified kinase often referred to as PDK2 or Ser 473 kinase.

Kinetic studies of PKB activation in the presence of CTMP can be carried out using COS-1 cells transfected with expression vectors for PKBα (2.5 μg of PHA.PKB) and CTMPs (5 μg of pF.CTMPs). After stimulation with 0.1 mM pervanadate (0, 1, 3, 9 and 15 minutes), immune kinase assays are performed in duplicate as described above. When CTMP is co-expressed with PKB, the activation of PKB after cell stimulation with pervanadate is strongly reduced (relative kinase activity being typically reduced by about 30% or more). Kinetic analysis of PKB activity in COS-1 cells revealed that the inhibition due to co-expressed CTMP can be overcome if the cells are stimulated for a long period. This gain of activation correlates with increased phosphorylation on residue 473 but also on residue 308. Thus, CTMP can interact with PKB and maintain PKB in an inactive, non-phosphorylated form by preventing its phosphorylation by upstream kinases in non-stimulated cells. This state could be regulated since the PKB/CTMP complex is no longer detectable after a 10 minute stimulation of cells with pervanadate under the conditions used here.

Example 10

Effect of Insulin or IGF-1 on CTMP Modulation of PKB Activity

To determine the effect of CTMP on PKBα activity in response to physiological stimuli, HEK-293 cells transfected with constructs expressing PKBα and increasing amounts of CTMP were treated with insulin or IGF-1. HEK293 cells were transfected with expression vectors for HA-PKBα (1 μg) and pF-CTMP (0, 1 or 5 Ag). Cells were serum-starved (24 h) and stimulated with either insulin (100 nM, 15 min.) or IGF-1 (50 nM, 10 min.) at 37° C. Cells were processed for immune-kinase assay as described in Example 9, as were the phosphorylation states of PKBα residues Ser473 and Thr308. Similar to data observed in COS-1 cells with pervanadate, PKBα kinase activity was stimulated by both insulin and IGF-1, and this stimulation was progressively inhibited by increasing levels of CTMP expression. Furthermore, analysis of the phosphorylation status of PKB revealed that CTMP expression led to a concomitant decrease in Ser473 and Thr308 phosphorylation induced by insulin and IGF-1. These data reinforce the results seen with pervanadate (Example 9), a more robust stimulator of PKB than either insulin or IGF-1, and strongly support the hypothesis that CTMP is an inhibitor of PKB in vivo.

To gain further insights into the negative regulation of PKBα function by CTMP, the effect of CTMP on PKBα-mediated transcriptional regulation was analysed. Results in our laboratory have revealed that PKBα strongly reduces both basal and serum-stimulated transcriptional activity of the c-fos promoter. HEK cells were transfected with 200 ng of the pfos-luc reporter gene together with pHA-PKB (200 ng) and pF-CTMP (1 μg) where indicated. Luciferase assays were performed 48 hours after transfection according to standard techniques (Promega luciferase assay kit). HEK cells were transfected with increasing amounts of pAS-CTMP (1, 2, 4 and 10 μg), an expression vector encoding an anti-sense CTMP cDNA. For the transfected anti-sense CTMP cDNA, oligonucleotides T7 and 5'-CTCATCMCACTCTGMCATT-3' (SEQ ID NO: 4) were used in RT-PCR reactions to distinguish the anti-sense construct from the endogenous CTMP cDNA. PKB expression and Ser473 phosphorylation were assayed by direct immuno-blotting. Levels of the anti-sense cDNA were measured by RT-PCR. Co-expression of CTMP completely abolished the inhibitory effect of PKBα on c-fos mediated transcription. Indeed, CTMP expression elevated c-fos promoter activity above control levels, an effect most likely due to inhibition of endogenous PKB. To determine the consequence of disrupting CTMP function in vivo, HEK293 cells were transfected with an anti-sense CTMP expression vector. Increasing amounts of anti-sense CTMP cDNA, confirmed by RT-PCR, increased Ser473 phosphorylation of endogenous PKB without changing its expression. These data demonstrate that inhibition of endogenous CTMP function increases the activation status of endogenous PKBα, and strongly suggests that CTMP acts as a negative regulator of PKBα in vivo.

Example 11

CTMP Modulation of PKB In Vivo: Phenotypical Reversion of PKB-Transformed cells by CTMP To establish that CTMP inhibits PKB in-vivo, CTMP is stably expressed in PKB-transformed cells, and CTMP expression is verified to revert the cells into a non-transformed phenotype. For this purpose, the AKT8-transformed CCL64 mink lung cell line (AKT8) can be used, which has been described to be transformed and tumorigenic in-vitro due to the presence of the v-Akt oncogene, the viral homologue of c-Akt/PKB (Staal et al., 1977, Proc. Natl. Acad. Sci. USA, 74, 3065-3067; Staal, 1987, Proc. Natl. Acad. Sci. USA, 84, 5034-5037; Staal and Hartley, 1988, J. Exp. Med., 167, 1259-1264).

AKT8 cells were transfected with expression vectors for CTMP ($CTMP_L$ and $CTMP_s$) and puromycin-resistant colonies were selected, amplified and tested for different criteria: cellular morphology, growth rate and in-vivo tumorigenesis. If CTMP is a PKB inhibitor, the AKT8 transformed cells might be phenotypically reverted to non-transformed CCL64 cells.

Both CCL64 and AKT8 cells are maintained in DMEM supplemented with 10% fetal calf serum (FCS, Life Technologies). Cells are stably transfected with CTMP as follows. Four 9 cm dishes of AKT8 transformed CCL64 cells are transfected with 15 μg of pSG5 (negative control, no puro-resistance gene), pSG5-FlagNt-puro (for selection of puromycine-resistant clones), PF.CTMPL or pF.CTMPs (for selection of puro-resistant and CTMP expressing clones), essentially as described above. After transfection, each plate is trypsinized and re-seeded on 3 plates in medium containing 2 μg/ml of puromycin. Emerging clones are selected after 7 days when they reach a size of about 100-500 cells, with pre-greased cylinders (Sigma chemicals), and transferred into 24 wells plates. The clones are then passed into 2 wells of a six well cluster. One well is used for screening for CTMP expression by Western-blot with the anti-flag antibody whereas the second well is passed into a 9 cm dish for freezing. The stable clones are then maintained in 10% FCS DMEM supplemented with 1 microg/ml of puromycin.

Selected puro-resistant clones (series 2B, 3C and 4A/B) and control cell lines CCL64/AKT8 are analyzed for CTMP and PKB expression using the anti-Flag and the anti-PKB PAb10 antibodies, respectively. CTMP expressing clones (3C4, 3C5, 3C8, 4A1, 4B2, 4B3, 4B4 and 4B5) exhibit different levels of CTMP expression, whereas v-PKB remains largely unchanged in all cell lines tested, including the AKT8 or puromycin-resistant 2B1 and 2B2 control cell lines. These data exclude the possibility that the altered properties of the CTMP expressing clones are due to a loss of the integrated v-PKB. Significantly, levels of endogenous PKBα in v-Akt transformed cells are dramatically up-regulated.

The presence of PKBα-CTMP complexes in vivo was examined by immunoprecipitation using both PKBα and CTMP specific antibodies. PKBα-CTMP complexes were detected using PKBα, or FLAG antibodies, in membrane fractions of AKT8 cells stably expressing FLAG-CTMP. Furthermore, v-Akt-CTMP complexes were also detected in this fraction, demonstrating that CTMP interacts with both forms of PKB expressed in these cells, and a conservation of interaction between PKB and CTMP proteins from different species.

To study the morphology of the cell lines expressing CTMP, cells are seeded in a 35 mm well of a six well cluster and photographed with a phase-contrast microscope before reaching confluency. The morphology of the clones is compared with that of the non-transformed parental CCL64 epithelial cells. CTMP expression clearly alters the morphology of the transformed cells: cells are larger and can form a mosaic as CCL64 does. Thus, CTMP alters the transformed morphology to a normal morphology showing that they can counteract v-akt activity in-vivo, at the morphological level. Interestingly, the cytoplasm of the cells from clones 4A1 and 4B4 are highly vacuolized, a phenotype identical to the one obtained when cells are treated with the PI-3K fungal inhibitor Wortmannin (Brown et al., 1995, J. Cell Biol., 130, 781-796).

To establish a growth rate curve of selected clones, $5 \times 10^4$ cells from selected cell lines are seeded in 35 mm wells of a six well cluster (Falcon) in duplicate. Cells are trypsinized at various time points and viable cells that excluded trypan blue are counted twice, at two different dilutions, in a Neubauer cell. Strikingly, all the morphologically reverted cell lines grow much more slowly compared to the control cell line (AKT8 and puro-resistant AKT8, 2B2 cells), thus showing that CTMP acts negatively on PKB-induced proliferation. Moreover, clones 3C4, 3C5, 4A1, 4B2, 4B3 and 4B5 grow much more slowly than the non-transformed CCL64 suggesting that CTMP has a strong inhibitory effect on v-Akt but also on endogenous c-Akt activated proliferation.

Example 12

CTMP Tumour Suppressor Action

The tumorigenicity of the reverted CCL64 clones of Example 11 is determined by sub-cutaneous injection of cells into nude mice (Table 1). Cells are trypsinized, washed and re-suspended in PBS at a concentration of $10^7$ cells/ml. 100 μl is then injected into the back of the nude mice, sub-cutaneously. The tumours are measured with callipers. The two diameters of the tumours measured with callipers are given for the indicated time (Table 1). Mice injected with 2B2 control cells developed tumours after 11 days, whereas mice injected with CTMP expressing clones exhibited at least a clear delay in tumour formation showing that CTMP expression also inhibits tumorigenic properties of v-Akt transformed cells. Tumour growth was abolished in four of seven CTMP expressing clones injected into nude mice. Taken together, these results show that CTMP can counteract PKB activity in-vivo and act as a tumour suppressor gene product that acts on PKB, delaying or abolishing tumour mass formation in mice.

All references referred to herein, as well as priority application GB 0014185.3 filed Jun. 6, 2000, are hereby incorporated by reference as if each were referred to individually.

TABLE 1

| Clones | days post-injection | | | | |
|---|---|---|---|---|---|
| | 11 | 14 | 20 | 22 | 24 |
| 2B2 | 2.4 × 2.4 | 3.5 × 4.2 | 4.8 × 5.8 | 6.0 × 6.5 | 8.6 × 10.5 |
| 3C4 | — | — | — | — | — |
| 3C5 | — | — | — | — | — |
| 3C8 | — | — | 3.2 × 3.2 | 3.4 × 3.7 | 4.5 × 4.5 |
| 4A1 | — | — | — | — | 3.1 × 3.5 |
| 4B2 | — | — | — | 4.2 × 4.2 | 4.0 × 4.5 |
| 4B3 | nd | nd | nd | nd | nd |
| 4B4 | — | — | — | — | — |
| 485 | — | — | — | — | — |

The invention claimed is:

1. An isolated nucleic acid comprising:
   (i) a nucleotide sequence as shown in SEQ ID NO:1 encoding carboxy terminal modulating protein, said protein having a protein kinase B binding activity, protein kinase B inhibiting activity, or tumor suppressive activity;
   (ii) a nucleotide sequence encoding carboxy-terminal modulating protein, said protein having a protein kinase B binding activity, protein kinase B inhibiting activity, or tumor suppressive activity, said nucleotide sequence differing from SEQ ID NO:1 by codon usage;
   (iii) a nucleotide sequence encoding a carboxy-terminal modulating protein homologue with at least 95% identity to SEQ ID NO:2, said protein homologue having a protein kinase B binding activity, protein kinase B inhibiting activity, or tumor suppressive activity, said nucleotide sequence differing from SEQ ID NO:1 by having at least one inserted, deleted or altered codon; or
   (iv) a nucleotide sequence fully complementary to the nucleotide sequences of (i), (ii) or (iii).

2. A recombinant vector comprising the nucleic acid of claim 1.

3. A recombinant vector comprising the nucleic acid of claim 1 wherein a polypeptide encoded by said nucleic acid is expressed in the form of a fusion protein.

4. An isolated host cell transformed with the recombinant vector of claim 2.

5. An isolated host cell transformed with a nucleic acid according to claim 1.

* * * * *

SEQUENCE LISTING

<160> NUMBER OF SEQ ID NOS: 6

<210> SEQ ID NO 1
<211> LENGTH: 1304
<212> TYPE: DNA
<213> ORGANISM: Homo sapiens
<220> FEATURE:
<221> NAME/KEY: CDS
<222> LOCATION: (47)..(769)

<400> SEQUENCE: 1

```
gaattcggca cgagctagag caagcgcggc cccgcggccc ggagcc atg ctg agg         55
                                                  Met Leu Arg
                                                    1 agc tgc gcc gcg cgc ctc cgc acg ctg ggg gct ctg tgc cgg ccg cca       103
Ser Cys Ala Ala Arg Leu Arg Thr Leu Gly Ala Leu Cys Arg Pro Pro
      5                  10                  15 gta ggc cgg cgc ctg ccg gga agc gag ccg cga ccc gag ctg agg tca       151
Val Gly Arg Arg Leu Pro Gly Ser Glu Pro Arg Pro Glu Leu Arg Ser
 20                  25                  30                  35 ttt tct tct gag gaa gtc att ctt aag gac tgt tct gtc ccc aac ccc       199
Phe Ser Ser Glu Glu Val Ile Leu Lys Asp Cys Ser Val Pro Asn Pro
                 40                  45                  50 agc tgg aac aag gac cta aga ctg ctc ttt gac cag ttt atg aag aaa       247
Ser Trp Asn Lys Asp Leu Arg Leu Leu Phe Asp Gln Phe Met Lys Lys
             55                  60                  65 tgt gaa gat ggc tcc tgg aaa cgt ttg cct tca tat aaa cgt aca cct       295
Cys Glu Asp Gly Ser Trp Lys Arg Leu Pro Ser Tyr Lys Arg Thr Pro
         70                  75                  80 act gaa tgg att caa gac ttc aaa acc cat ttt ctt gac cca aag ctt       343
Thr Glu Trp Ile Gln Asp Phe Lys Thr His Phe Leu Asp Pro Lys Leu
     85                  90                  95 atg aaa gaa gaa caa atg tca cag gcc cag ctc ttc acc aga agc ttt       391
Met Lys Glu Glu Gln Met Ser Gln Ala Gln Leu Phe Thr Arg Ser Phe
100                 105                 110                 115 gat gat ggc ctg ggc ttt gaa tac gtg atg ttc tac aat gac att gag       439
Asp Asp Gly Leu Gly Phe Glu Tyr Val Met Phe Tyr Asn Asp Ile Glu
                120                 125                 130 aaa agg atg gtt tgc tta ttt caa gga ggc cct tac ctg gaa gga cca       487
Lys Arg Met Val Cys Leu Phe Gln Gly Gly Pro Tyr Leu Glu Gly Pro
            135                 140                 145 cct gga ttc att cat gga ggt gcc att gca acc atg att gat gct act       535
Pro Gly Phe Ile His Gly Gly Ala Ile Ala Thr Met Ile Asp Ala Thr
        150                 155                 160 gtt ggt atg tgt gca atg atg gct ggg gga atc gtc atg act gcc aat       583
Val Gly Met Cys Ala Met Met Ala Gly Gly Ile Val Met Thr Ala Asn
    165                 170                 175 ctc aac atc aat tat aaa aga cct atc cct ctt tgt tct gtt gtt atg       631
Leu Asn Ile Asn Tyr Lys Arg Pro Ile Pro Leu Cys Ser Val Val Met
180                 185                 190                 195 ata aat agc caa ctt gat aaa gtt gaa gga agg aaa ttt ttt gtt tcc       679
Ile Asn Ser Gln Leu Asp Lys Val Glu Gly Arg Lys Phe Phe Val Ser
                200                 205                 210 tgt aat gtt cag agt gtt gat gag aag acc cta tac tca gag gcg aca       727
Cys Asn Val Gln Ser Val Asp Glu Lys Thr Leu Tyr Ser Glu Ala Thr
            215                 220                 225 agc tta ttt ata aag ctg aat cct gct aaa agt ctg aca taa               769
Ser Leu Phe Ile Lys Leu Asn Pro Ala Lys Ser Leu Thr
        230                 235                 240 agagctgctg gtgaactcca tctcattctc gcccctccag aagaagcagt tgtcccccaa     829
atactctgct ccctcactgc tgaatccctg tagggagaag cctgccaaca gtgaccttcc     889
gaaacagcct tctgaataca aagaggattc agtttccatc ttctcaactt tttaacacag     949
aaacacttcc tgcagcata tcgacaactc tcgggcagg cgctgtggct cacacctgta     1009
atcccagcac tttaggaggc cgaggcaggc ggattgcctg agctcaggag ttcaagatca    1069
gtctgggcaa cacgatgaaa ctccgtctct actaaaatac aaaaaattat ccaggcatgg    1129
tggcgtacgc ctgtagtccc agctactcag gaggctgagg caggagaatt gcttgaaccc    1189
```
aggaggaaga ggttgcagtg agccaagatc atgccacatc actccaacct gggcaacaga    1249
acaagaaccc atctcaaaca aaacaacaaa caaaaaaaaa aaaaaaaact cgaga          1304

<210> SEQ ID NO 2
<211> LENGTH: 240
<212> TYPE: PRT
<213> ORGANISM: Homo sapiens

<400> SEQUENCE: 2

```
Met Leu Arg Ser Cys Ala Ala Arg Leu Arg Thr Leu Gly Ala Leu Cys
  1               5                  10                  15

Arg Pro Pro Val Gly Arg Arg Leu Pro Gly Ser Glu Pro Arg Pro Glu
             20                  25                  30

Leu Arg Ser Phe Ser Ser Glu Val Ile Leu Lys Asp Cys Ser Val
         35                  40                  45

Pro Asn Pro Ser Trp Asn Lys Asp Leu Arg Leu Leu Phe Asp Gln Phe
     50                  55                  60

Met Lys Lys Cys Glu Asp Gly Ser Trp Lys Arg Leu Pro Ser Tyr Lys
 65                  70                  75                  80

Arg Thr Pro Thr Glu Trp Ile Gln Asp Phe Lys Thr His Phe Leu Asp
                 85                  90                  95

Pro Lys Leu Met Lys Glu Gln Met Ser Gln Ala Gln Leu Phe Thr
            100                 105                 110

Arg Ser Phe Asp Asp Gly Leu Gly Phe Glu Tyr Val Met Phe Tyr Asn
        115                 120                 125

Asp Ile Glu Lys Arg Met Val Cys Leu Phe Gln Gly Gly Pro Tyr Leu
    130                 135                 140

Glu Gly Pro Pro Gly Phe Ile His Gly Gly Ala Ile Ala Thr Met Ile
145                 150                 155                 160

Asp Ala Thr Val Gly Met Cys Ala Met Met Ala Gly Gly Ile Val Met
                165                 170                 175

Thr Ala Asn Leu Asn Ile Asn Tyr Lys Arg Pro Ile Pro Leu Cys Ser
            180                 185                 190

Val Val Met Ile Asn Ser Gln Leu Asp Lys Val Glu Gly Arg Lys Phe
        195                 200                 205

Phe Val Ser Cys Asn Val Gln Ser Val Asp Glu Lys Thr Leu Tyr Ser
    210                 215                 220

Glu Ala Thr Ser Leu Phe Ile Lys Leu Asn Pro Ala Lys Ser Leu Thr
225                 230                 235                 240
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:CTMP primer

<400> SEQUENCE: 3
tctgaggaag tcattcttaa g                                                 21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:CTMP primer

<400> SEQUENCE: 4

```
ctcatcaaca ctctgaacat t                                            21

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:IL-1a primer

<400> SEQUENCE: 5
gtctctgaat cagaaatcct tctatc                                       26

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:Il-1a primer

<400> SEQUENCE: 6
catgtcaaat ttcactgctt catcc                                        25
```